US00RE36201E

United States Patent [19]

Miller

[11] E Patent Number: Re. 36,201

[45] Reissued Date of Patent: Apr. 27, 1999

[54] HIGH ENERGY X-Y NEUTRON DETECTOR AND RADIOGRAPHIC/TOMOGRAPHIC DEVICE

[76] Inventor: Thomas G. Miller, 254 Brentwood La., Madison, Ala. 35758

[21] Appl. No.: 08/842,512

[22] Filed: Apr. 23, 1997

Related U.S. Patent Documents

Reissue of:

[64] Patent No.: 5,410,156
Issued: Apr. 25, 1995
Appl. No.: 08/106,437
Filed: Aug. 13, 1993

U.S. Applications:

[63] Continuation-in-part of application No. 07/964,455, Oct. 21, 1992, abandoned.

[51] Int. Cl.[6] ..... G01N 23/222

[52] U.S. Cl. ..... 250/390.04; 250/390.11

[58] Field of Search ..... 290/390.04, 390.11, 290/390.12, 390.02, 390.03, 391, 370.05

[56] References Cited

U.S. PATENT DOCUMENTS 5,200,626 4/1993 Schultz et al. .
5,278,418 1/1994 Broadhurst .

FOREIGN PATENT DOCUMENTS 3108687 5/1991 Japan .

OTHER PUBLICATIONS

Article, "Guidelines for Preparing Responses to the Federal Aviation Administrations Broad Agency Announcement (BAA) for Aviation Security Research Proposals TCBAA 90–001", Federal Aviation Administration Technical Center, New Jersey, Revision 3–Nov. 1, 1989 (Cover page & pp. 2–15).

Article, "Determination of H, C, N, O Content of Bulk Materials from Neutron–Attenuation Measurements", J.C. Overley Int. J. Radiat. Isot., vol. 36, No. 3, pp. 185–191, 1985.

"Nuclear–Based Techniques for Explosive Detection", T.Gozani, R.Morgado, C.Seher, Journal of Energetic Materials, vol. 4, pp. 377–414 (1986).

"Airport Tests of SAIC/FAA Explosive Detection System Based on Thermal Neutron Activation Technique", P.Shea and T.Gozani, American Defense Preparedness Assoc. Proceedings, Cambridge, MA, Oct. 26, 1988.

(List continued on next page.)

*Primary Examiner*—Edward P. Westin
*Assistant Examiner*—Richard Hanig
*Attorney, Agent, or Firm*—Baker & Botts, L.L.P.

[57] ABSTRACT

An improved fast neutron x-y detector and radiographic/tomographic device utilizing a white neutron probe (4). The invention includes a multiple scattering filter (44), radiographic and tomographic imaging of the number densities of atoms in small volume increments through a sample 32 and the atomic, chemical and physical structure of a sample, (32), and neural net analysis techniques, where the neural net is trained through use of simulated volume increments. The invention detects fast neutrons over a two dimensional plane, measures the energy of the neutrons, and discriminates against gamma rays. In a preferred embodiment, the detector face is constructed by stacking separate bundles (6) of scintillating fiber optic strands (20) one on top of the other. The first x-y coordinate is determined by which bundle (6) the neutron strikes. The other x-y coordinate is calculated by measuring the difference in time of flight for the scintillation photon to travel to the opposite ends of the fiber optic strand 20. In another embodiment, the detector is constructed of discrete scintillator sections (48) connected to fiber optic strands (52) by couplers (50) functioning as lens. The fiber optic strands (52) are connected to a multi-anode photomultiplier (100) tube (56). The x-y coordinate of a neutron interaction is determined by the row and column of the affected scintillation section (48). Neutron energy for both detectors is calculated by measuring the flight time of a neutron from a point source (2) to the detector face.

39 Claims, 15 Drawing Sheets

OTHER PUBLICATIONS

"Multi–dimensional Neutron–compound Tomography Using Cooled Charge–coupled Device", IEEE Transactions on Nuclear Science, vol. 38, No. 2, Apr. 1991.

"Element–Sensitive Computed Tomography with Fast Neutrons", by J.C. Overley, Nuc. Instr. and Meth. In Physics Research, B24/25 (1987), pp. 1058–1062.

"A Pressurized Multi–Wire Proportional Chamber for Neutron Imaging", IEEE Transactions on Nuclear Science, vol. NS–25, No. 1, Feb. 1978, pp. 558–561.

"PFNA Technique for the Detection of Explosives", Proc. Of First Int. Symp. On Explosives Det. Technology, FAA Tech. Ctr., Atlantic City Int. Airport, NJ, Feb. 1992.

SIDE

FRONT

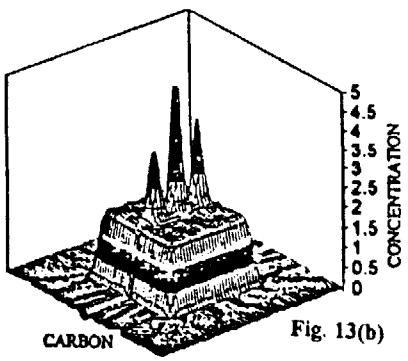
Fig. 13(a)
Fig. 13(b)
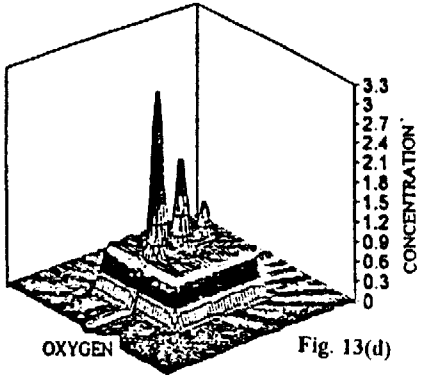
Fig. 13(c)
Fig. 13(d)
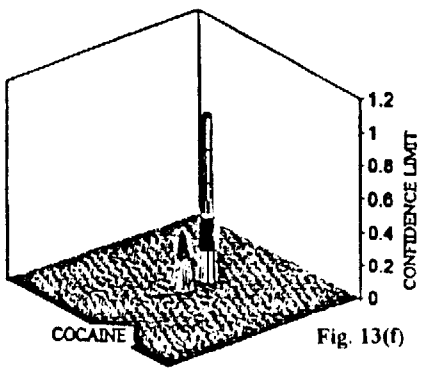
Fig. 13(e)
Fig. 13(f)

HIGH ENERGY X-Y NEUTRON DETECTOR AND RADIOGRAPHIC/TOMOGRAPHIC DEVICE

Matter enclosed in heavy brackets [ ] appears in the original patent but forms no part of this reissue specification; matter printed in italics indicates the additions made by reissue.

CROSS-REFERENCE

This application is a continuation in part of that certain patent application "High Energy X-Y Neutron Detector and Radiographic Device," Ser. No. 07/964,455, filed on Oct. 21, 1992, now abandoned.

FIELD OF INVENTION

This invention relates to a device and method of determining the presence of substances in a sample through neutron radiographic/tomographic imaging of the number densities of atoms in the sample, and more particularly to the detection of explosives.

BACKGROUND ART

1. Fast Neutron Radiographic and Tomographic Systems

A workable system for detecting explosives in airport luggage is urgently needed. A very small piece of modern explosive will destroy and airplane. These explosives are easy to hide and cannot be detected by current systems. For example, a plastic explosive hidden in a small radio apparently destroyed Pan American Flight 103 over Lockerbie, Soctland. The most accurate method would be a tomographic scan which could identify the elements which make up an explosive. For practical use in an airport, each scan would have to be completed in seconds. A system this advanced does not exist and is not possible under current technology.

Current methods for detecting explosives in airport luggage use uncharged particles such as X-rays and neutrons. X-rays are sensitive to differences in X-ray absorption coefficients in the luggage. However, explosives have absorption coefficients similar to many items commonly found in luggage. For this reason, detection systems using X-rays have high false alarm rates. X-ray computed tomography (CT) scanners are also used to inspect luggage. However, CT scanners are also sensitive to X-ray absorption coefficients, and so have the same problems as X-ray systems.

The most common nuclear based explosive detection methods are thermal neutron absorption (TNA) and n, gamma pulsed fast neutron spectroscopy. "Nuclear-Based Techniques for Explosive Detection", T. Gozani, R. Morgado, C. Seher, Journal of Energetic Materials, Vol. 4, pp. 377–414 (1986). The TNA detects the n, gamma reaction on nitrogen, and so searches only for nitrogen. "Airport Tests Of SAIC/FAA Explosive Detection System Based On Thermal Neutron Activation", P. Shea and T. Gozani, American Defense Preparedness Assoc. Proceedings, Cambridge, Mass., Oct. 26, 1988. TNA has an unacceptably high false alarm rate, since many materials other than explosives contain large amounts of nitrogen. Other problems with TNA include that the neutrons must be thermalized, the n, gamma cross section is in the millibarn range, it is difficult to obtain the spatial nitrogen concentration, and the background count is very high.

N, gamma pulsed spectroscopy detects the neutron inelastic scattered gamma rays from nitrogen, carbon, and oxygen.

Zdzisaw Sawa and Tsahi Gozani, (PFNA Technique for the Detection of Explosives), Proc. of First Int. Sym. on Explosives Det. Technology, FAA Tech. Ctr., Atlantic City Int. Airport, N.J., Feb. 1992. Problems with n, gamma spectroscopy include that the cross sections are still in the millibarn range, the background counts are very high, determination of concentration as a function of position has large uncertainties, and it is difficult to make a gamma ray detector with adequate energy resolution and still maintain high count rate capability.

TNA and n, gamma spectroscopy search for explosives in an indirect way. Both cause a neutron interaction and then attempt to detect the resulting gamma rays. Neither method accurately pinpoints the location of an explosive in the luggage. A system is needed which can probe directly for explosives through first order interactions.

The most accurate method would be a tomographic scan which could identify the number densities of the dements which make up explosives in small volume increments through the luggage. Neutrons are an ideal probe, because neutrons interact directly with the atomic nuclie in the sample. A tomographic method which uses total cross sections rather than partial cross sections would be optimal. Current methods using neutron probes detect only second order effects such as gamma rays (partial cross sections) and do not provide tomographic images.

In conventional neutron tomography, neutrons are directed through a sample and the result are recorded on a detector. E. W. McFarland, R. C. Lanza and G. W. Poulos, "Multi-dimensional Neutron-computed Tomography Using Cooled, Charged-coupled Devices," IEEE Transactions on Nuclear Science, Vol. 38, No. 2, Apr. 1991. A number of runs at different angles are used to create a tomographic image. Conventional methods reconstruct the spatial distribitions of macroscopic interaction cross sections from the attenuation of radiation passing through the sample.

These conventional methods use monoenergetic neutron probes. Monoenergetic probes show macroscopic cross-section variations, while providing little information regarding atomic or chemical structure. In contrast, a white neutron probe (fast neutrons of multiple energies) would provide information not possible from a monoenergetic neutron probe. Light provides a simple analogy. Under a red light (single energy), all objects appear as shades of red. However, a white light (multiple energies) reveals different colors and other details. A tomographic system using a white neutron probe would be far more advanced than any system in operation. Unfortunately, under current technology, it cannot be built. Problems include multiple scattering of radiation, inability to detect and measure the energies of fast neutrons over an x-y plane, and difficult in reducing and analyzing data. These numerous problems would have to be solved in a single system.

Overly discussed that, under laboratory conditions, it is possible to identify different elements in a sample by using a white neutron beam. J. C. Overly, "Determinations of H, C, N and O content of Bulk Materials from Neutron Activation Measurements," Int J. Radiat Isot., Vol. 36, No. 3, pp. 185–191, 1985. Overly also discussed the scientific principle in deducing the number densities of elements along a neutron beam for a tomographic cut. "Element-Sensitive Computed Tomography With Fast Neutrons" by J. C. Overly, Nuc. Instr. and Meth. in Physics Research, B24/25 (1987) 1058–1062.

Overly required 23 hours for a single cut. A workable system for detecting explosives must reduce this time to seconds. Even after 23 hours, Overly obtained only an estimate of number densities at a single cut. A workable system must obtain a tomographic image of the number densities of atoms over the entire suitcase in a matter of seconds. As Overly acknowledged in his paper, current technology has not advanced to the point of applying these scientific principles in a workable system. The Federal Aviation Association ("FAA") recognized this critical need when requesting proposals for an invention using a white neutron probe for explosives. FAA "Guidelines for Preparing Responses to the Federal Aviation Administration's Broad Agency Announcement For Aviation Security Research Proposals.", p. 7, Nov. 1989. The FAA Guidelines acknowledge that the scientific principle has not been applied to airline security, even though it has been published for several years. In fact, the scientific principle has not been applied to any workable system. Neither the FAA, nor any other party, has found a way to address all of the problems which must be solved in order for a white neutron probe system to work. The following sections describe these problems.

2. Multiple-Scattering Correction of Radiation

Neutron tomographic systems must detect neutrons from the source while excluding neutrons scattered by the sample. If scattered neutrons reach the detectors, the tomographic image will not be accurate. X-ray systems use a detector located behind a shielded slot only a few millimeters wide. The slot is narrow enough to exclude most scattered radiation. This is one reason why a CAT scan takes so long. The detector row moves slowly across the body. A system using a large detector array could view the entire sample at once. However, such detectors (if they existed) could not be used for tomography until the multiple scattering problem is solved. The problem is even more critical when designing a system using a white neutron probe. The system must detect, measure the energies, and catalog the location of millions of neutrons passing through different parts of a sample each second. In order to provide meaningful data, the spatial resolution must be as small as several centimeters square. A workable system must eliminate multiple scattering while completing a scan in only a few seconds. There is a critical need for such a system.

Harding, Pat. No. 4,380,817 (1983) attempted to correct multiple scattering for purposes other than tomography. Harding's method measures electron density in a body through radiation which is "single scattered" from a narrow pencil beam of radiation. Harding's method shields the detector from the single scattered radiation, so that the detector measures only multiple scattered radiation. Then the multiple scattered radiation is subtracted from the sum of the single and multiple scattered radiation. This method is not workable for neutron tomography, which requires measuring neutrons which are not scattered (either single or multiple scattered). Harding's system would not work in a system using a white neutron probe for tomography.

3. X-Y Position Fast Neutron Detectors

A tomographic system using a white neutron probe must detect fast neutrons passing through a sample and pinpoint the location in the sample for each neutron. The system must perform these functions for millions of neutrons striking all portions of the sample each second.

One solution is to place the sample in front of an x-y detector which can record the two dimensional (x-y) coordinates of neutron interactions. The points of interaction on the x-y detector correspond to the locations in the sample. There are x-y neutron detectors, but most are for thermal neutrons. (Neutrons which have a kinetic energy of approximately 0.025 electron volts.) Many types of x-y detectors use an element that has a large fission cross section for thermal neutrons. The fission fragments are detected through the ionization they produce. McFarland, cited above, describes a detector using a sheet of $^{6}$Lif-ZnS. Lithium-6 has a large fission cross section for thermal neutrons. A fraction of the incident thermal neutrons interact with the Lithium-6 to produce Lithium-7. The Lithium-7 in turn fissions into a triton and an alpha particle, which cause a scintillation. A CCD camera records the scintillation and its position. Another variation uses an element that absorbs the thermal neutrons and emits X-rays or gamma rays.

The above types of detectors have a low detection efficiency for fast neutrons, since the fast neutron fission cross section is very small. Also, current x-y detectors cannot perform all of the functions needed for a tomographic system using a white neutron probe. These functions include measuring neutron energy, achieving high count rates, and collecting data in a way to facilitate tomographic imaging.

Fast neutron x-y detectors do exist, but have certain drawbacks. One type of x-y detector uses the multi-wire proportional counter with s proton radiator. B. Director, S. Kaplin and V. Perez-Mendez, "A Pressurized Multi-Wire Proportional Chamber for Neutron Imaging," IEEE Tr. on Nucl. Sc., Vol. NS-25, No. 1, Feb. 1978, 558–561. The proton radiator is a thin sheet of a hydrogen rich material such as polyethylene. A fraction of the incident neutrons scatter from the protons in the radiator. The resulting recoil protons enter the multi-wire proportional counter. The multi-wire proportional counter consists of thin gas filled cells with small wires running parallel throughout the cells. The wires are placed at high voltage. When a proton enters a cell close to a particular wire, a voltage pulse is created.

By recording the position of the voltage pulse, the position of the event is known in the direction perpendicular to the wires. By placing a second ionization chamber with wires running perpendicular to the first set of wires, the position in the other direction is known. The radiators must be very thin so that the recoil protons can escape. In order to achieve reasonable efficiency, many units must be placed in tandem. This setup cannot efficiently count neutrons below 3 MeV, since the radiator would require a width of nearly zero to allow the lower energy protons to reach the first cell. Efficiency would approach zero. These detectors do not allow measurement of neutron energy and would not provide the high count rates or neutron energy resolution required for a white neutron probe system.

An x-y detector for fast neutrons could be constructed from a large number of individual photomultiplier tubes. The applicant describes such a detector in "Contraband Detection Device", Ser. No. 07/635,996 filed on Dec. 31, 1990. One problem with this detector is that its electronics are very complex. A complete detector system is required for each photomultiplier tube. For example, a detector face of only 400 cm. by 400 cm., with a spatial resolution of 4 cm. by 4 cm., would require one hundred 4 cm. by 4 cm. detectors to form a single row 400 cm. long. One hundred rows of such detectors would provide a surface of 400 cm. by 400 cm. The system would require 10,000 individual detectors and 10,000 complete electronics systems. The system would be highly complex and expensive. Another problem is that the array is rigid and not capable of being geometrically configured for the optimal shape.

4. Collection, Reduction and Analysis of Data

Identifying contraband in sealed luggage is one of the most difficult tasks facing scientists. Explosives and drugs contain the same elements as most other items usually found in luggage. These elements include hydrogen (H), carbon (C), nitrogen (N) and oxygen (O). Explosives do contain characteristic ratios of these elements. However, in order to identify these ratios, a tomographic system would have to search an entire suitcase over small volume increments with an uncertainty of only a few percent. These tasks present enormous problems under current technology. Two problems, multiple scattering and measuring radiation over an x-y plane, were discussed above. In addition, the tomographic system would have to gather, reduce, and analyze data for millions of neutron interactions per second. The entire scan must be completed in seconds. The system must distinguish neutrons from gamma rays. New methods of data reduction and analysis would have to be developed for such a system to function with the speed and accuracy required for an airport system.

In summary, there are no tomographic systems which use a white neutron probe. There are numerous problems, unsolved under current technology, which prevent the operation of a workable system. These problems include multiple scattering of neutrons, detecting fast neutrons over a two-dimensional plane, calculating energies of the neutrons, and collecting, reducing and analyzing the data, all under circumstances when millions of neutrons will be incident on the sample and detector each second. The entire analysis of each sample must be completed in seconds. Such a system does not exist and cannot be built under current technology.

Objects and Advantages

Accordingly, several objects and advantages of my invention are as follows.

One object is to obtain a tomographic/radiographic image of the number densities and ratios of atoms over small volume increments in a sample.

Another object of the invention is to obtain the tomographic/radiographic image within a matter of seconds.

Yet another object is to gather, reduce, analyze the data, and make a determination whether an explosive or other contraband is present in the sample, all within a matter of seconds.

A further object is to achieve high neutron count rates.

Yet another object is to eliminate or reduce multiple scattering of neutrons from the sample.

Still another object is to determine the two dimensional location of the unscattered neutrons passing through the sample.

Another object of the invention is to measure the energies of unscattered neutrons passing through the sample.

A still further object is to distinguish gamma rays from neutrons.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

DRAWING FIGURES

FIGS. 13a–f show an output spectrum of the invention's neural net analysis of a sample obtained during practice of the invention.

Figure 14:
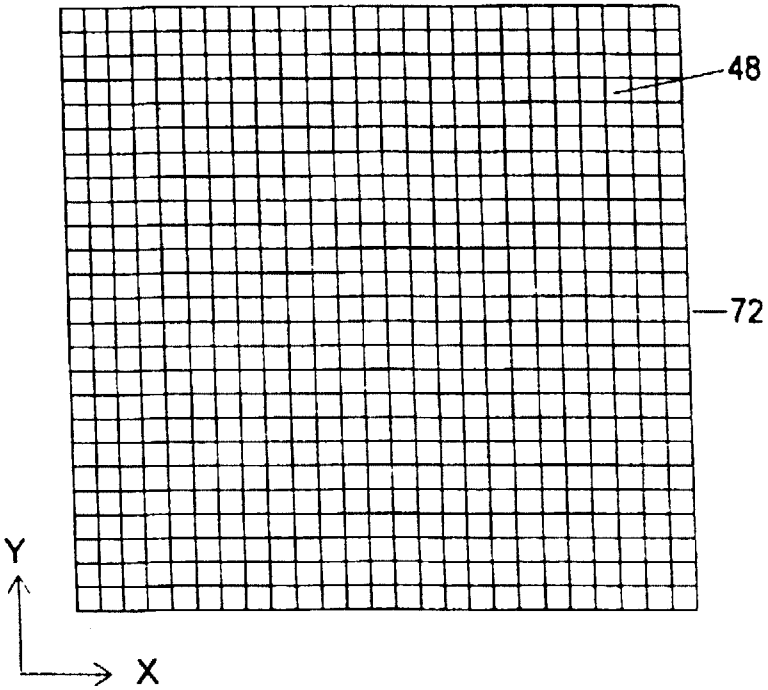
Figure 14:
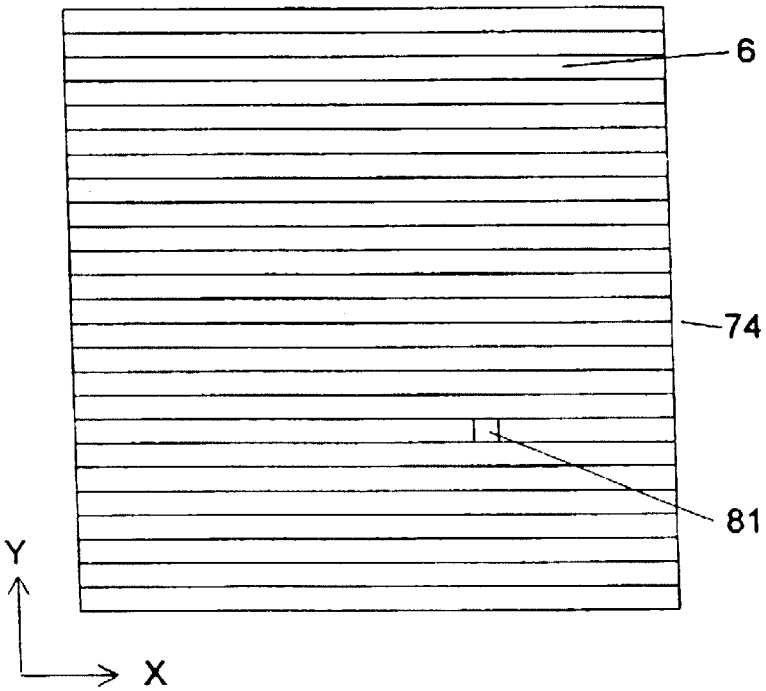

FIGS. 14a–b show how the tomographic device determines the x-y position of a neutron interaction using the strip detector and array detector.

Figure 15:
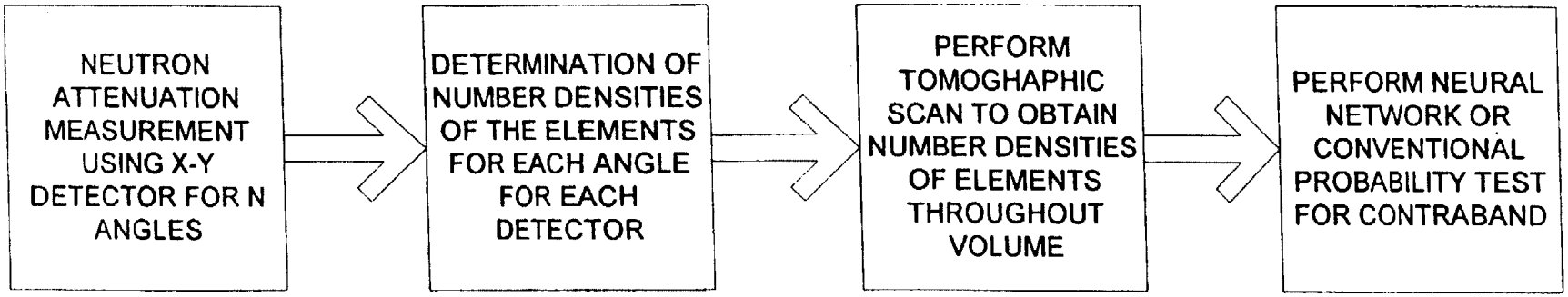

FIG. 15 shows a flow chart providing an overview of the tomographic imaging and analysis method.

| Reference Numerals in Drawings | |
|---|---|
| 2 | pulsed white neutron source |
| 4 | pulsed white neutron beam |
| 5 | neutrons which have passed thru sample |
| 6 | fiber optic bundle of strip detector |
| 8 | couplers for strip detector (This embodiment includes four couplers, 8A, 8B, 8C, 8D.) |
| 10 | photomultiplier tubes for strip detector (This embodiment includes four tubes, 10A, 10B, 10C, 10D.) |
| 12 | voltage cable for photomultiplier tubes and signaling cabling for electronics for strip detector |
| 14 | electronics for strip detector |
| 15 | electronics for array detector |
| 16 | computer |
| 18 | output screen printout |
| 20 | individual scintillating fiber optic strands inside a bundle for strip detector |
| 21 | bonding material fastening together scintillating fiber optic strands into a bundle for strip detector |
| 22 | second time to amplitude converter for strip detector |
| 24 | first time to amplitude converter for strip detector |
| 26 | first or/sum circuit for strip detector |
| 28 | sum circuit for strip detector |
| 30 | second or/sum circuit for strip detector |
| 31 | turntable |
| 32 | sample |
| 34 | anticoincidence circuit for strip detector |
| 36 | time or beam pick-off unit |
| 37 | pulsed accelerator |
| 38 | time pick-off unit for strip detector |
| 40 | beam target |
| 42 | delay for strip detector |
| 44 | multiple scattering filter |
| 46 | opaque cladding for scintillator section for array detector |
| 48 | plastic scintillator section of array detector |
| 50 | scintillator - fiber optic coupler/lens for array detector |
| 52 | non-scintillating fiber optic cable for array detector |
| 54 | fiber optic - anode coupler for array detector |

-continued

| | Reference Numerals in Drawings |
|---|---|
| 56 | multianode photomultiplier tube for array detector |
| 57 | voltage divider for array detector |
| 58 | single anode of multianode photomultiplier tube for array detector |
| 59 | discriminator for array detector |
| 60 | signaling cabling - array detector |
| 61 | or circuit - array detector |
| 62 | ion source |
| 64 | radiation shield |
| 66 | luggage conveyor track with turntable |
| 70 | x-y detector (which may comprise 72 or 74) |
| 72 | array detector |
| 74 | strip detector |
| 76 | hollow passage through multiple scattering filter |
| 78 | solid segment of multiple scattering filter |
| 80 | flight path of neutrons from point source to x-y detector face |
| 81 | x position virtual detector of strip detector |
| 84 | time to amplitude converter for array detector |
| 86 | time pick off unit for array detector |

DESCRIPTION—FIGS. 1–14

Figures Incorporating the Entire Invention

Figure 1:
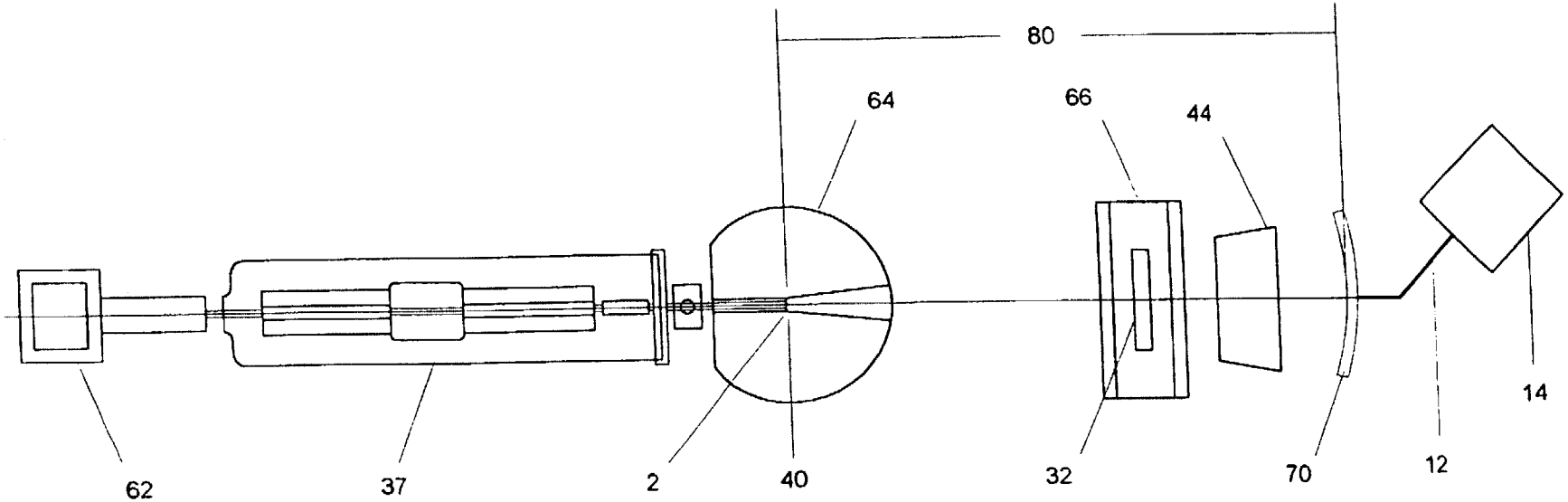
FIG. 1 shows the entire tomographic device in its preferred embodiment for purposes of orientation, with more details in later figures.

FIG. 1 shows an overall view of the preferred embodiment of the tomographic device as an airport explosives detection system. A pulsed white neutron source 2, created by a pulsed accelerator 37, provides a beam of white neutrons. In its preferred embodiment, the detector surface has a radius of curvature equal to the distance from the neutron source 2 to an x-y detector 70. The detector is a square about one meter by one meter. The pulsed white neutron beam 4 contacts a sample 32. A conveyor track 66 conveys the sample 32 onto a turntable 31 in front of the x-y detector 70. Neutrons 5 passing through the sample contact a multiple scattering filter 44. Neutrons which are not scattered and which pass through the filter 44 contact the x-y detector 70. A conventional computer (shown in FIG. 4), such as an IBM 486 personal computer, stores data from the x-y detector 70 in a specific memory bank.

Figure 2:
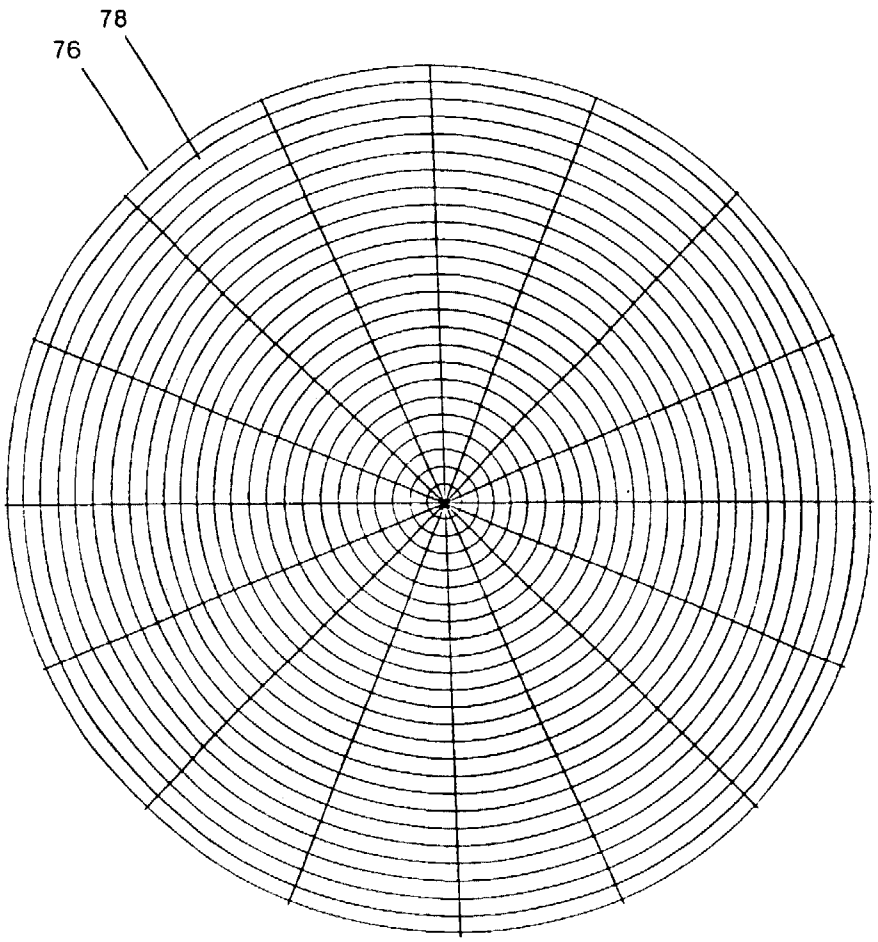
FIG. 2 shows a detail of the multiple scattering filter.
Figure 2:
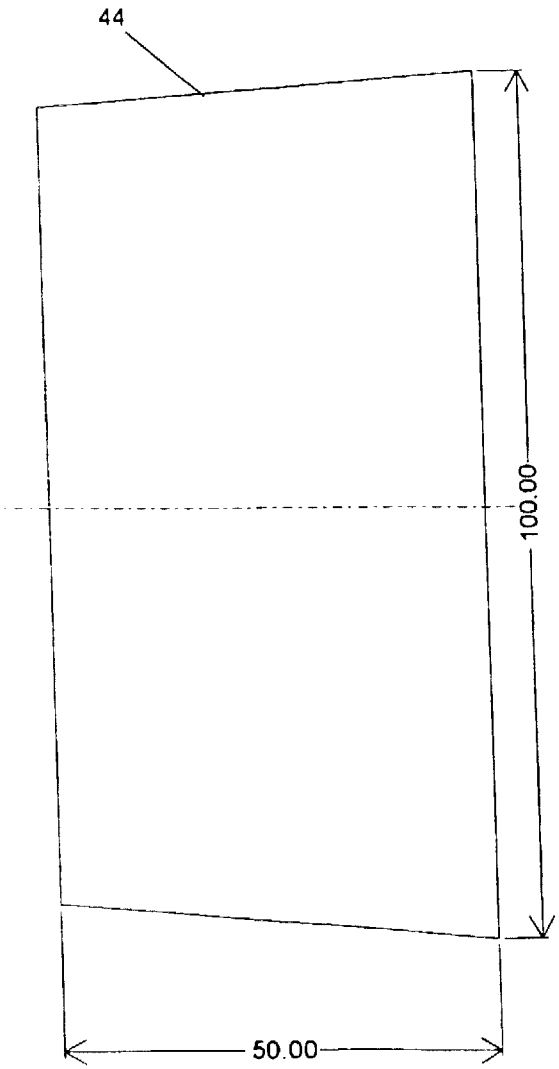

FIG. 2 shows front and side views of the filter 44, which consists of a frustum of a cone with alternating sections in a "dartboard" configuration along is axis, with the sections alternating between hollow passages 76 and solid segments 78. In its preferred embodiment, the filter 44 is constructed of polyethylene or other neutron attenuating material and is approximately 0.5 meters thick. The hollow passages 76 lie along straight lines from the neutron point source and perpendicular to the face of a detector.

Figure 3:
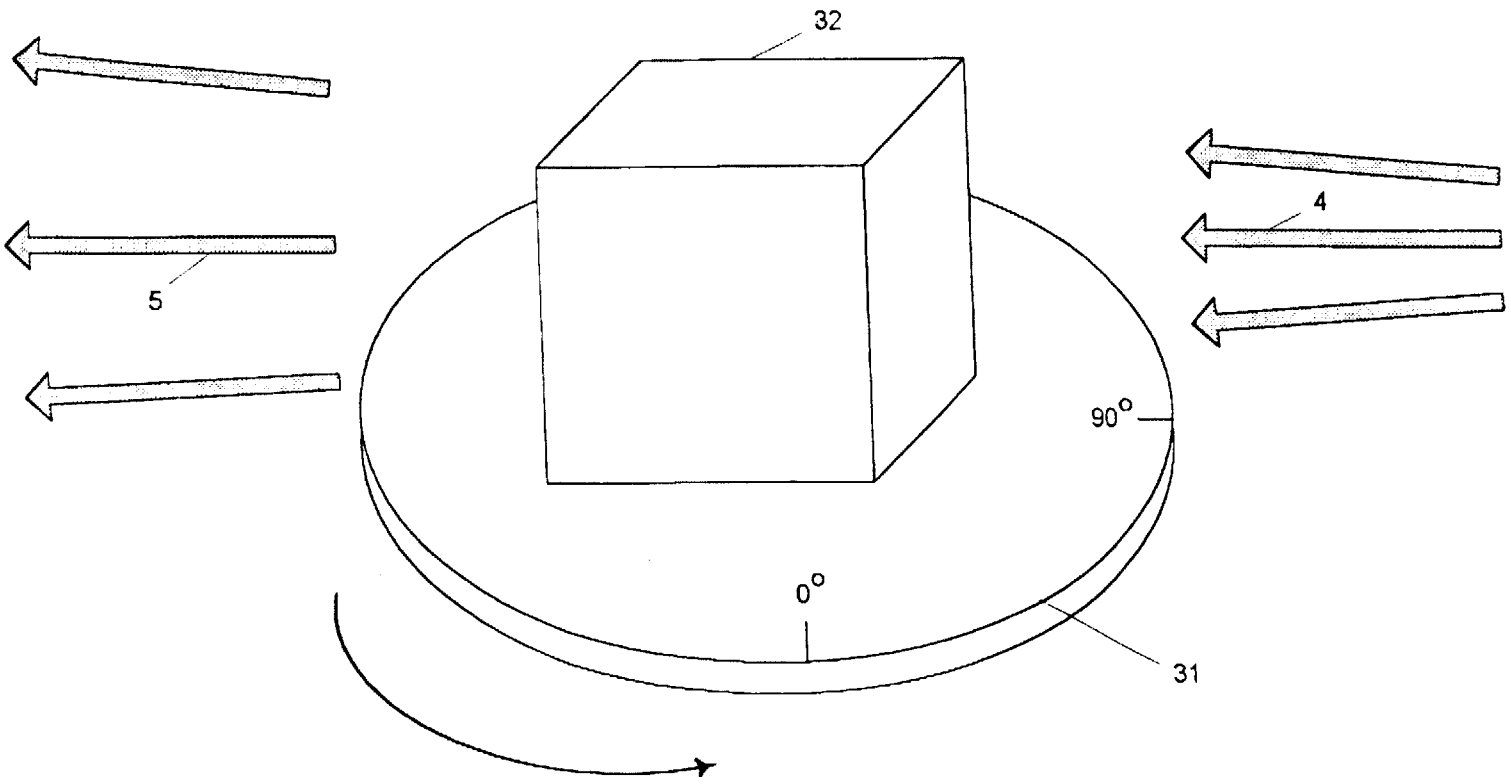
FIG. 3 shows a sample on a turntable.

FIG. 3 shows a sample 32 on a turntable 31. The pulsed white neutron beam 4 strikes the sample 32. Views are taken at designated angles from 0° to 180° or 0° to 360° and the data stored in the memory bank of the computer 16.

Figures Incorporating the Strip Detector

Figure 4:
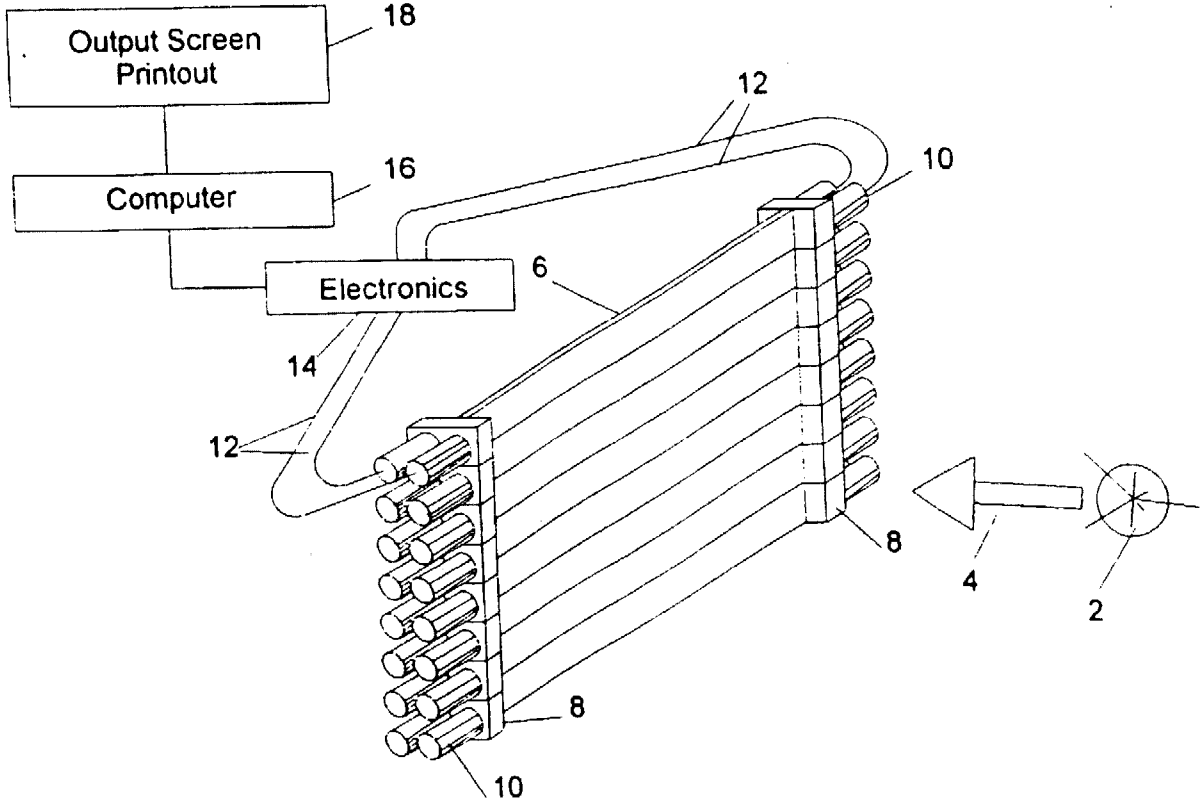
FIG. 4 shows the setup for the tomographic device using the strip detector.

FIG. 4 shows an overall view of the strip detector array. For purposes of orientation, a pulsed white neutron source 2 provides a beam of white neutrons 4. The strip detector consists of bundles 6 of one or more scintillating fiber optic strands 20 (shown in FIG. 5). Each bundle 6 is attached to four couplers 8, two at each end, which attach four photomultiplier tubes 10, two at each end. Cabling 12 is attached to the photomultiplier tubes for voltage and signaling. The signaling cabling is directed to the electronics 14, which in turn is connected to a specific memory bank in a computer 16 and output 18 such as a computer monitor. Electronic devices and computer programs are readily available to process and store information from the photomultiplier tubes 10 and electronics 14. A common analog-to-digital converter is the PCA II available from Tennelec Co., Oak Ridge, Tenn.

Figure 5:
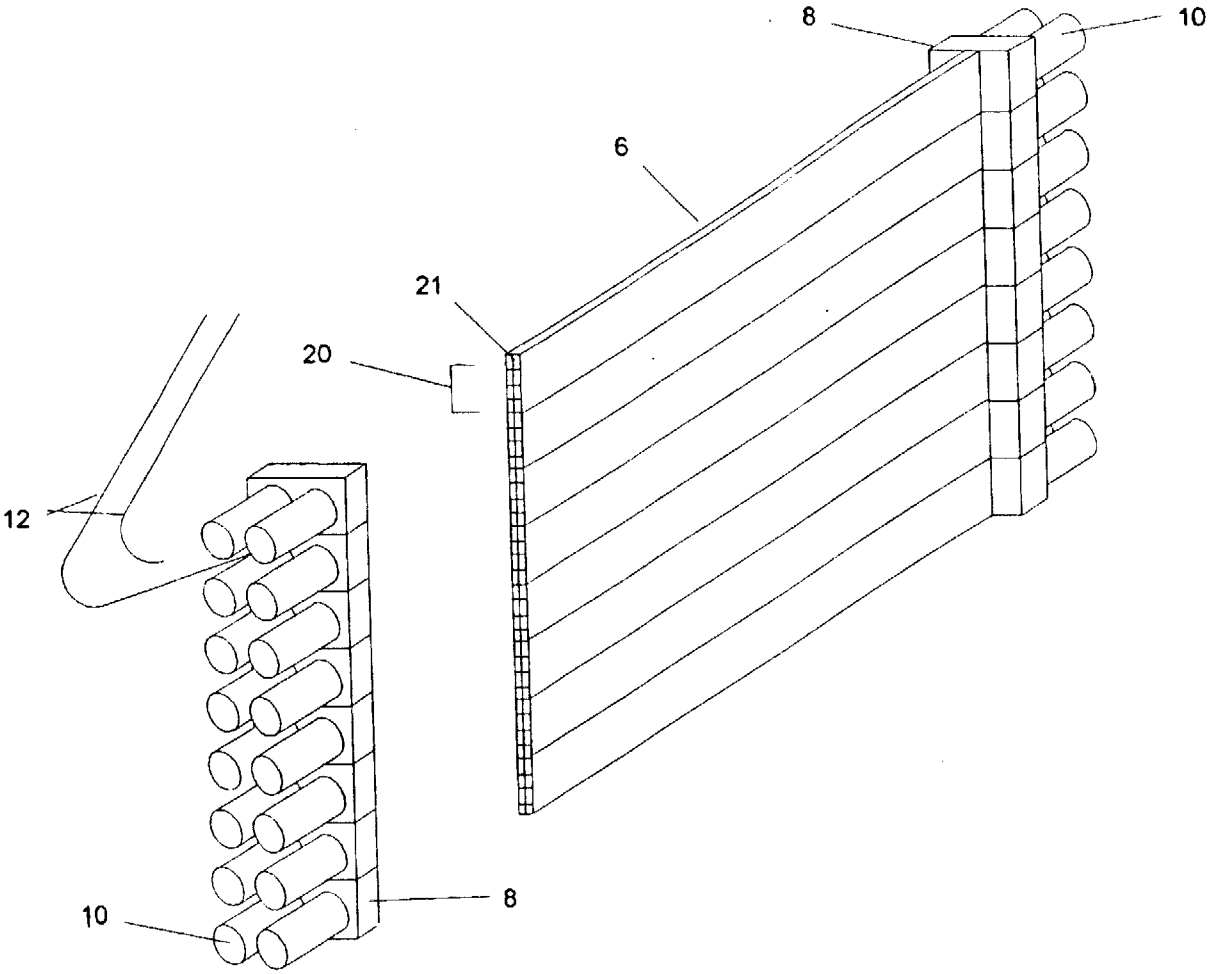
FIG. 5 shows the face of the strip detector with a view of the bundles.

FIG. 5 shows the strip detector and a detail of the strands 20 comprising the bundles 6. A white neutron beam 4 is shown for purposes of orientation. The bundles are 1 cm. in width by 4 cm. in height, although the size of the bundles may vary according to the use of the strip detector. Each strand 20 is square and can range from 300 microns by 300 microns up to the actual size of the strip. Each strand 20 is a light pipe. The strands 20 are constructed from a plastic scintillator rich in hydrogen, such as BC 404. This type of scintillator is readily available on the commercial market from vendors including Bicron Corp., Newbury, Ohio. The strands 20 contain cladding with density less than the scintillator, which provides internal reflections for photon scattering angles less than the "critical angle." Each bundle is attached to another by a bonding means 21 such as a commercially available glue. Each bundle 6 is connected to four couplers 8, which couple each end of the individual strands 20 into one of four photomultiplier tubes 10 attached to each bundle 6. The cabling 12 attached to each photomultiplier tube 10 supplies voltage and signaling cables to the electronics 14 (not shown) for the detector.

Figure 6:
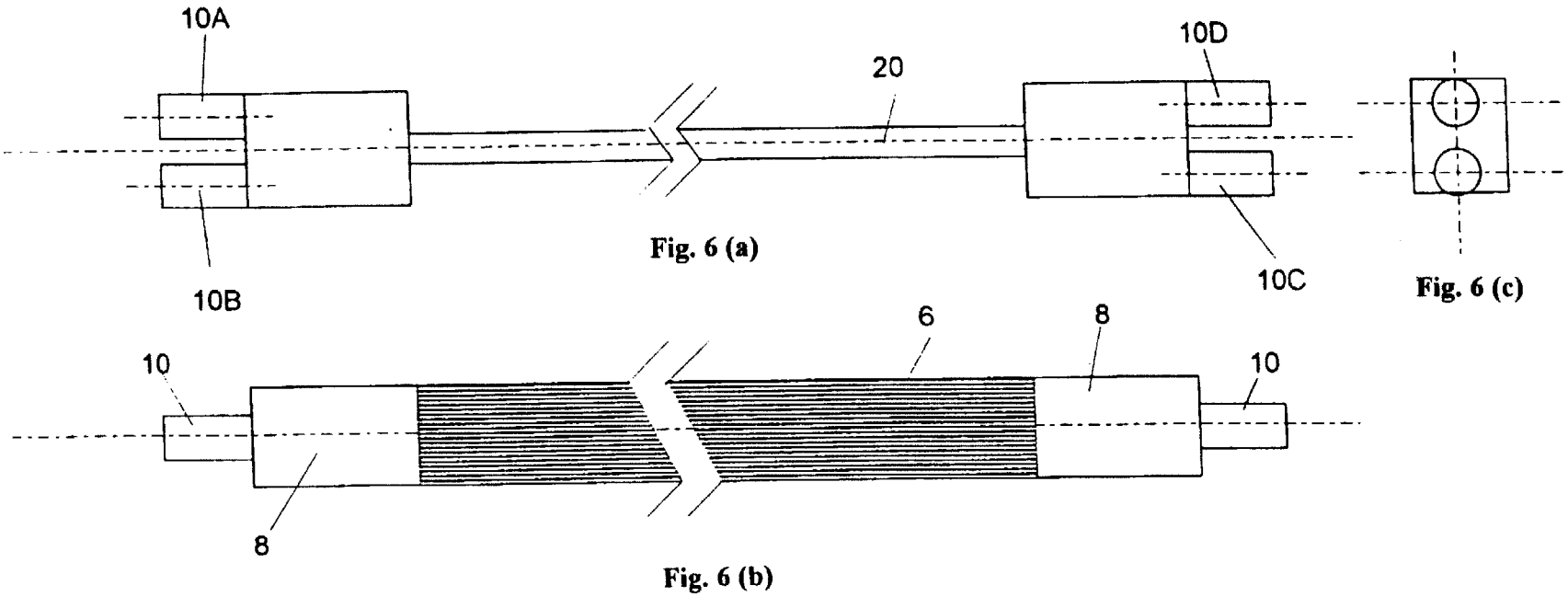
FIG. 6 shows the arrangement of a single bundle of the strip detector with four photomultiplier tubes attached.

FIG. 6 shows one bundle 6 and how the individual strands 20 of the strip detector are connected to four photomultiplier tubes 10 A–D through an alternating array. The strands 20 connected to photomultiplier tube 10A are connected to photomultiplier tube 10D and strands 20 connected to photomultiplier tube 10B are connected to photomultiplier tube 10C. Each strand 20 connected to photo multiplier tubes 10A and 10D are surrounded by four strands 20 connected to photomultiplier tubes 10B and 10D.

Figure 7:
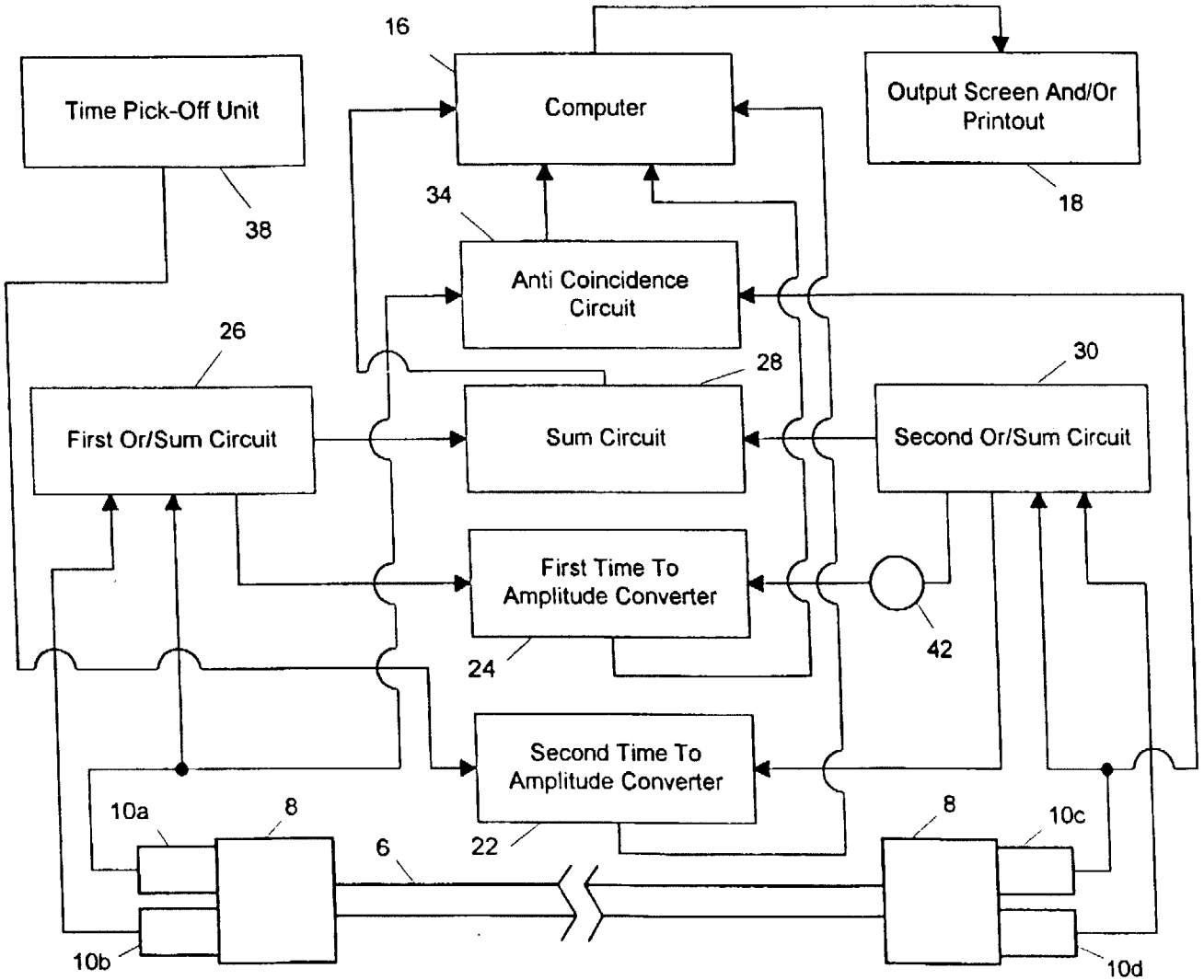
FIG. 7 shows the electronics system and circuits for one bundle of the strip detector.

FIG. 7 shows two or/and circuits 26, 30 and one sum circuit 28 which are used as logic units in the circuit diagram. The or/sum circuits 26, 30 can each be used as or circuits and sum circuits either simultaneously or individually. Outputs from photomultiplier tubes 10A and 10C go to the inputs of an anticoincidence circuit 34. An output from the anticoincidence circuit 34 indicates detection of a neutron. Outputs of photomultiplier tubes 10A and 10B go to the input of or/sum circuit 26. Outputs of photomultiplier tubes 10C and 10D go to the input of or/sum circuit 30. The sum output of or/sum circuit 26 gives the sum of the light coming out of one end of the bundle, while the sum output of or/sum circuit 30 gives the sum of the light coming out of the other end of the bundle 6. The sum outputs of or/sum circuits 26, 30 are summed by sum circuit 28, which gives the total amount of light coming from the bundle and can be used as a side condition to eliminate pulses that are too small or too large. The or output of or/sum circuit 26 goes to the start input of time-to-amplitude converter (TAC) 24. The or output of or/sum circuit 30 goes to the stop input of TAC 24 through a delay 42. The output of TAC 24 is used to determine the x coordinate of the neutron scattering event. The or output of or/sum circuit 30 goes to the start input of TAC 22. The stop input for TAC 22 comes from the time pick-off 38. The output of TAC 22 is used to determine the energy of the incident neutrons. The outputs of TAC 22, TAC 24, sum circuit 28 and anticoincidence circuit 34 are input into a general purpose computer 16 into specific memory banks for recording and processing.

Figure 8:
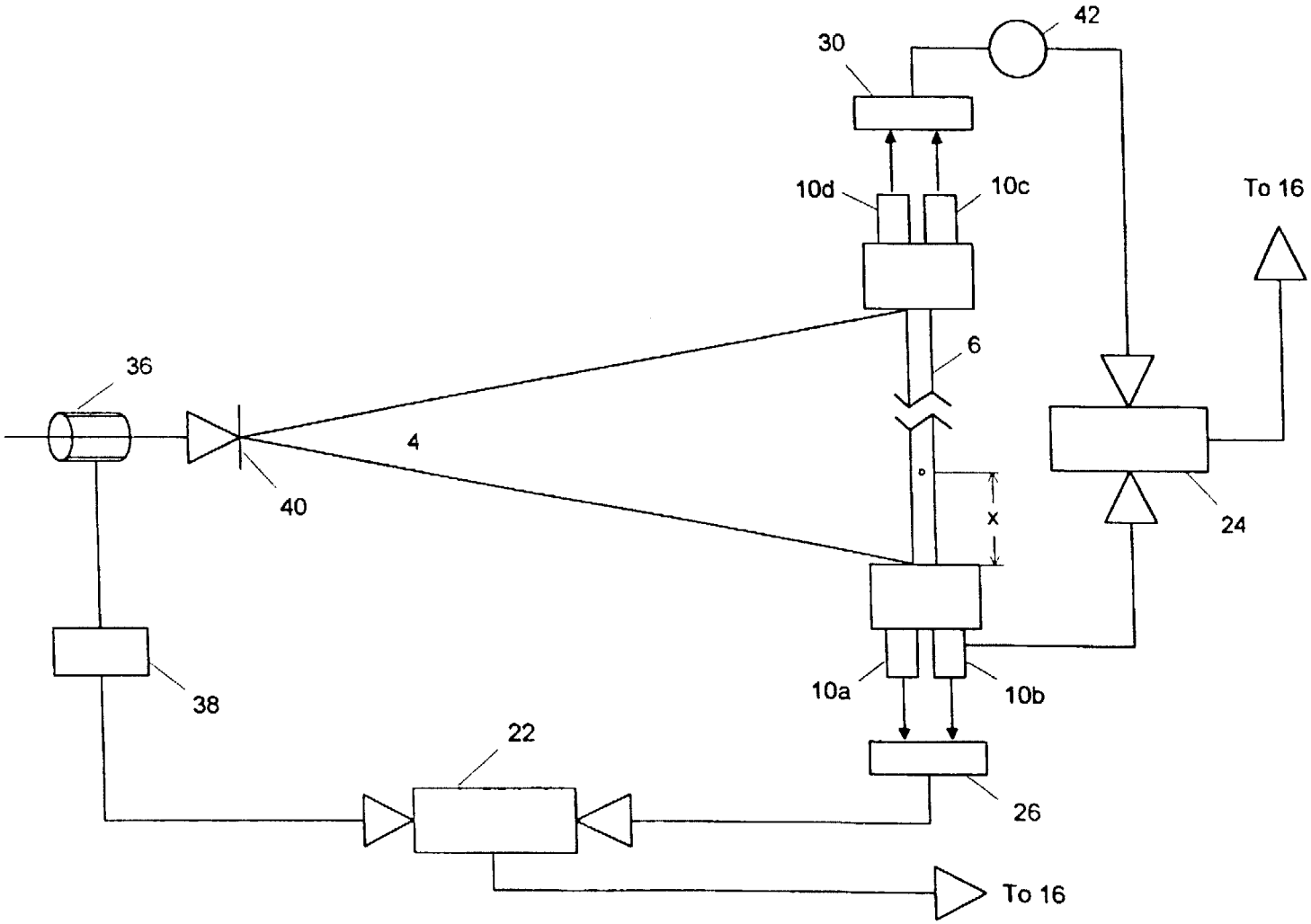
FIG. 8 shows how the tomographic device when using the strip detector calculates the two dimensional placement and energy of a neutron.

FIG. 8 shows that two time-to-pulse height converters TAC 22 and TAC 24 measure neutron energy and the position of neutron interactions in the bundle. TAC 24 measures the time difference between the pulses coming from the bundles 6. The tomographic device calculates the x position of the interaction based upon this time difference. TAC 22 measure the time of flight of each neutron detected over a known flight path. The tomographic device calculates the energy of the neutron based upon the time of flight and known flight path.

Figures Incorporating the Array Detector

Figure 9:
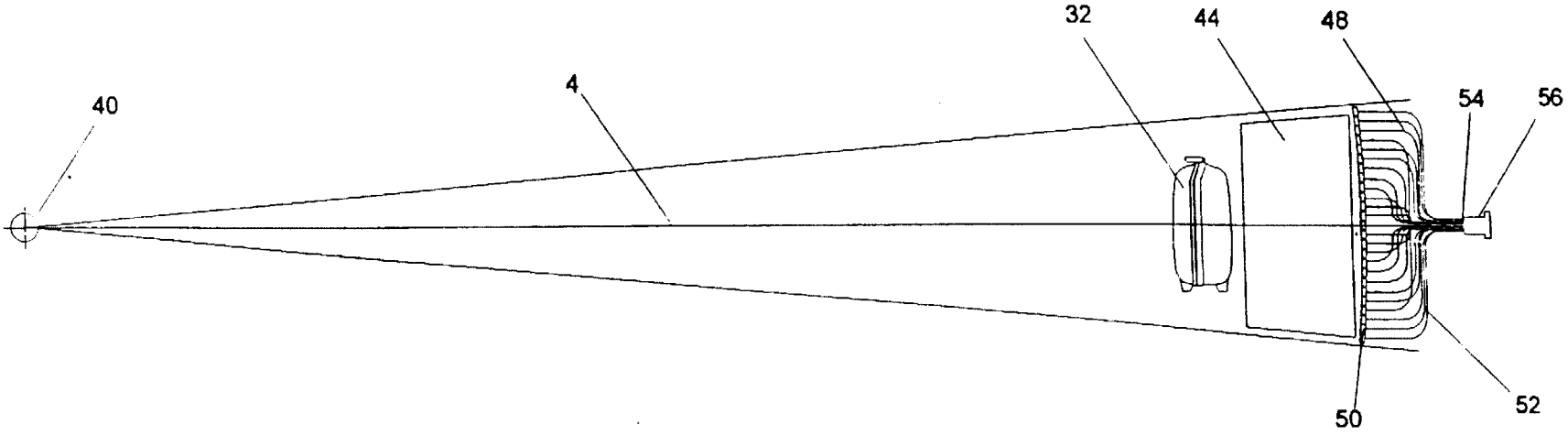
FIG. 9 shows a perspective view of the tomographic device when used with the array detector.

FIG. 9 shows an overall view of the array detector setup. A pulsed accelerator creates a beam of white neutrons 4 from a beam target 40. The white neutron beam 4 passes through a sample 32 and contacts the filter 44. Neutrons which are not scattered or absorbed pass through the hollow passages 76 of the filter 44 and contact the array detector. The array detector consists of discrete plastic scintillator sections 48. The sides of the plastic scintillator sections 48 are opaque to light through application of an opaque material 46 such as electrician's tape. The entire detector array is approximately 1 meter high and 1 meter long. Each scintillator section 48 is attached to a fiber optic cable 52 by means of a coupler 50. Each cable 52 is attached by means of a coupler 54 to a multi-anode photomultiplier tube 56.

Figure 10:
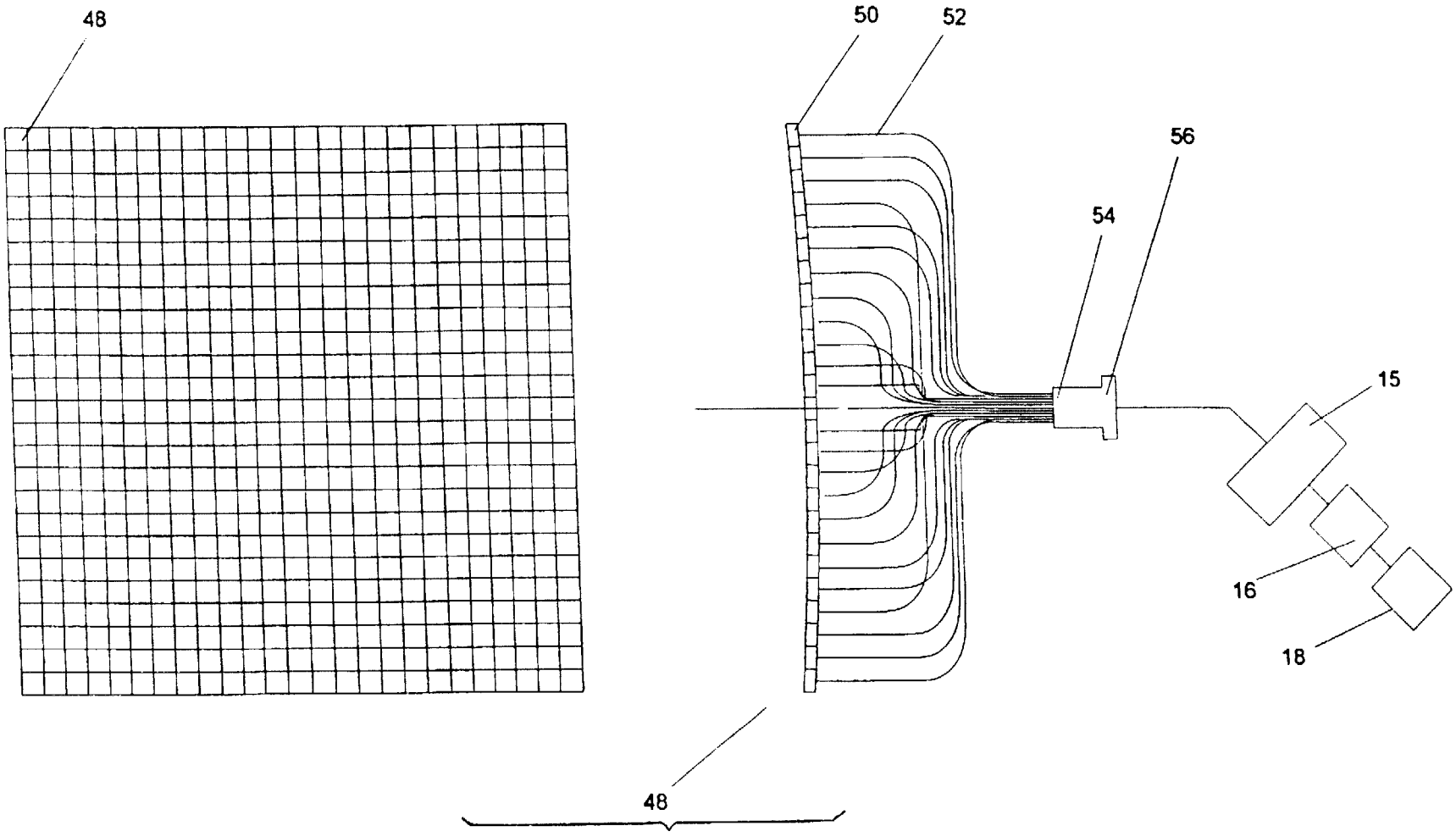
FIG. 10 shows a perspective of the array detector.

FIG. 10 shows the array detector. The face of the detector consists of scintillator sections 48. The scintillator sections 48 are approximately 2 cm. by 2 cm. wide and 1 cm. thick (which dimensions may be adjusted according to the spatial resolution desired). Each scintillator section 48 approximates a section of the inside of a sphere with a radius of curvature equal to the flight path. Each scintillator section 48 is connected by means of a scintillator-fiber optic coupler 50 to a non-scintillating fiber optic cable 52. Such coupler 50 is constructed as a lens to focus light energy into the light pipe. Each cable 52 is a light pipe constructed from a fiber optic cable. This type of fiber optic cable is readily available on the commercial market. Each cable 52 is connected to one anode of a multi-anode photomultiplier tube 56. The multi-anode tube 56 includes cabling 12 for voltage and signaling. The signaling cabling is directed to the electronics 15, which in turn is connected to a specific memory bank in a computer 16 and output 18 such as a computer monitor. Electronic devices and computer programs are commercially available to process and store information from the multi-anode tube 56 and for processing through the electronics 15.

Figure 11B:
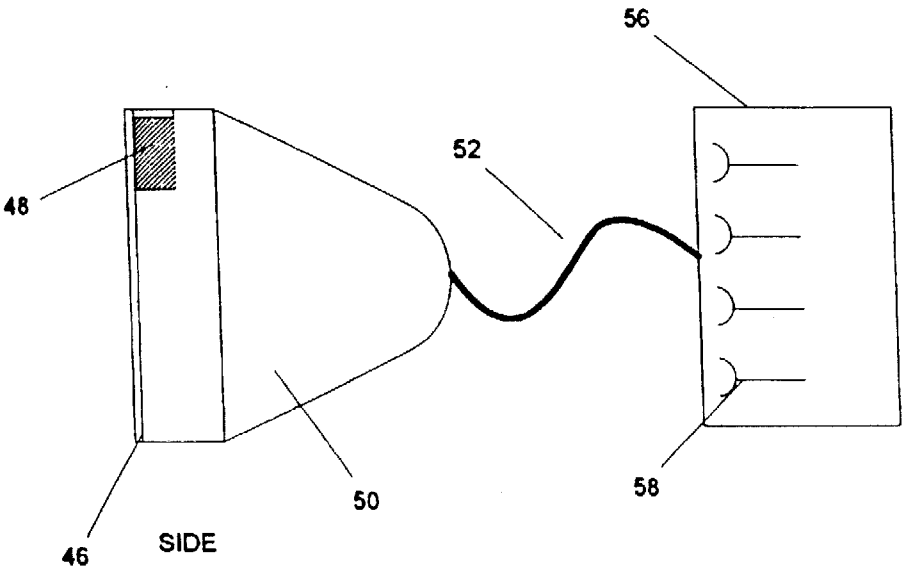
FIG. 11 shows a detail of one scintillator section of the array detector.
Figure 11A:
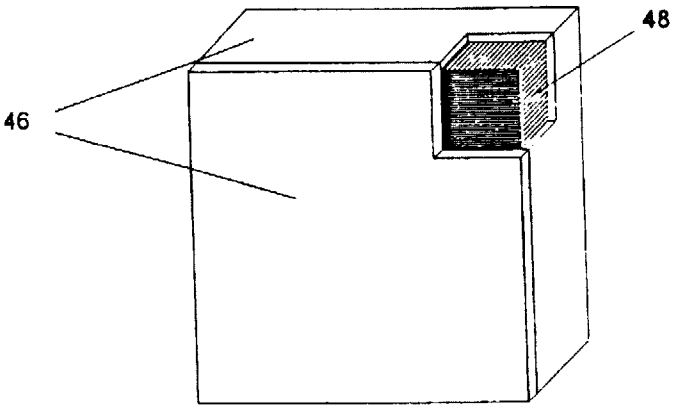

FIG. 11 shows one scintillator section 48 of the array detector and how the scintillator section 48 is connected to a coupler 50 constructed as a lens to focus light energy into the cable 52, which in turn is connected to the anode of the multi-anode tube 56. The sides of each scintillator section 48 are covered by opaque cladding 46.

Figure 12:
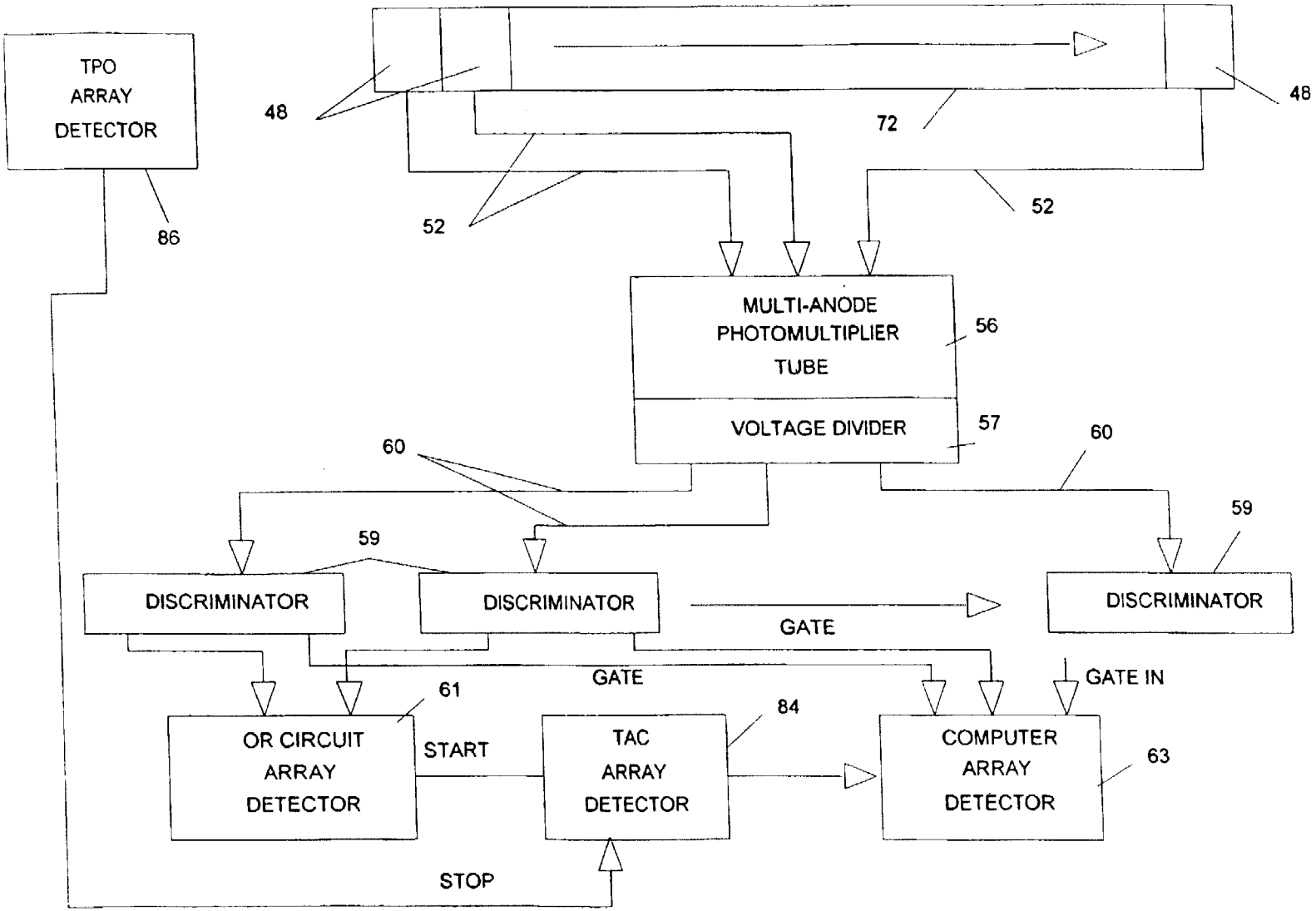
FIG. 12 shows the electronics system and circuits for one scintillator section of the array detector.

FIG. 12 shows the electronics for the array detector. Each scintillator section 48 is connected to the anode of a multi-anode tube 56 via cables 52. The multi-anode tube 56 and its voltage divider 57 convert light pulses from the scintillator sections 48 into electrical voltage pulses. The voltage pulses are fed through connecting cables 60 to discriminators 59. Two voltage pulses are created by each discriminator 59. One voltage pulse is fed to or circuit 61, which in turn is fed to the start input of time-to-amplitude (TAC) 84. The time-pick-off 86 provides the stop input to TAC 84. The second output from the discriminator 59 is fed to a gate input of the array detector computer 16 for storage of that particular TAC pulse in a section of memory reserved for that scintillator section 48.

FIG. 13 shows tomographic images created by the invention showing explosives and drugs hidden in a suitcase. The suitcase contains polyurethane, cocaine, and C-4 explosive. Polyurethane is used as a decoy because it is nitrogen-rich and difficult to distinguish from drugs or explosives. The suitcase is 60 cm. wide by 60 cm. long. The C-4 explosive, polyurethane, and cocaine, each with dimensions of 2 cm. by 3 cm., are in the middle of the suitcase. FIGS. 13a, 13b, 13c, and 13d show respectively the distributions of H, C, N, and O at a tomographic cut through the suitcase at the suspected location. FIG. 13e shows the neural network output of its confidence limit that explosives are present at the cut. As shown in FIG. 13e, when instructed to search only for explosives, the tomographic device finds the explosives but ignores the polyurethane and cocaine. FIG. 13f shows the output when the neural network searches for drugs. As shown in FIG. 13f, when instructed to search only for drugs, the tomographic device correctly identifies the drugs and ignores both the explosives and polyurethane. The tomographic device is able to search for explosives and drugs simultaneously. As shown in FIG. 13, the invention finds the small amounts of explosives and drugs hidden in a suitcase even when hidden behind a nitrogen rich decoy.

FIG. 14a shows how the tomographic device determines the x-y position of a neutron interaction using the strip detector. The vertical (y) position is identified by the bundle 6 in which the neutron interaction occurs. The horizontal (x) position of the neutron interaction is determined by measuring the difference in time which it takes a photon to travel to opposite ends of the strand 20. The spatial resolution of the strip detector 74 constitutes a "virtual" detector 81.

FIG. 14b shows that for the array detector, the x-y position of a neutron interaction corresponds to the row and column of the affected scintillator section 48.

FIG. 15 provides a flowchart of the tomographic process and neural net analysis in general terms.

Operation of Invention

1. Overview

A pulsed white neutron beam 4 is produced at a point source. The white neutron beam 4 is incident on an x-y detector 70 (two such detectors 72 and 74 are described in the present invention). A computer 16 records a baseline measurement of neutron energies without a sample in the beam. A conveyor track 66 then moves a sample 32 onto a turntable 31 into the beam path in front of the x-y detector 70. The white neutron beam 4 is directed at the sample 32. The filter 44 prevents neutrons scattered in the sample from reaching the x-y detector. A portion of the non-scattered neutrons travel through the hollow passages 76 in the filter 44 and contact the x-y detector 70. The tomographic device records the two dimensional positions and the energies of these neutrons. The tomographic device compares the transmitted beam to the original baseline beam. The tomographic device then determines neutron attenuation as a function of neutron energy through this comparison. The tomographic device then compares the resulting neutron attenuation curves with known total neutron cross sections to determine the elements/cm$^2$ in the neutron beam path that caused the specific neutron attenuation curves in the transmitted beam.

If the invention uses its tomographic option, the procedure is the same except that the invention rotates the sample 32 on the turntable 31. The tomographic device performs multiple scans of the sample at different angles. The tomographic device then inputs the resulting number densities into a tomographic program to determine the number densities of H, C, N and O per cm$^3$ at designated cuts along the sealed container. The tomographic device uses information from several cuts to create three dimensional distributions of H, C, N and O through the sample. The invention determines the ratios of H, C, N, and O for each small volume increment separately. The invention then applies its neural net methods to determine whether any of the volume increments contains an explosive. If H, C, N and O are present in the applicable ratios, the tomographic device sounds an alarm that an explosive is found. The following description describes certain aspects of the invention in more detail.

2. Correction of Multiple Scattering

The tomographic device contains a multiple scattering filter 44. The filter 44 allows neutrons to contact the detector only if the neutrons pass through the sample 32 without scattering. In the embodiment shown, the filter 44 is comprised of a frustum of a solid cone constructed of polyethylene (or other neutron attenuating material). The filter 44 is placed between the sample 32 and the x-y detector 70. The narrow end of the frustum faces the white neutron source. The frustum is divided into a "dartboard" configuration. The sections of the "dartboard" are alternating solid segments 78 and hollow passages 76 through the frustum along its axis. Each hollow passage 76 is constructed along a straight line from the white neutron source 2 and perpendicular to the face of the x-y detector 70. In this way, a neutron will cross a hollow passage only by traveling directly from the point source.

The filter 44 rotates and so the sample 32 is uniformly irradiated. In one embodiment the filter 44 is rotated by attaching a grooved track along the outside circumference of the filter 44. A conventional fan belt is placed in the groove and attached to a pulley on a conventional electric motor. In the preferred embodiment, the sample 32 will remain in the beam for 8–10 seconds. The neutron flight time for the tomographic device is at most 400 nanoseconds, while the filter 44 rotates only a few times per second. Hence, the filter 44 is essentially still during the flight of any specific neutron. In this way, a neutron at the point source "sees" either a solid segment or a hollow passage of the filter. A neutron that "sees" a hollow passage will proceed to the sample towards that hollow passage. If the neutron is not scattered, it will travel through the sample, through the hollow passage, and will contact the x-y detector.

3. Operation of Strip Detector

A. Detection of Fast Neutrons

In the manner described above, unscattered neutrons will contact a bundle 6 of the strip detector 74. Certain neutrons will strike a scintillator strand 20 and scatter from hydrogen (protons). The protons will recoil in the strand 20 and emit light energy. A wavelength shifter is mixed in the scintillator. This type of scintillator is commercially available, such as BC 404 manufactured by Bicron Corporation. A fraction of this light is trapped by the strand 20 and travels (in both directions) to photomultiplier tubes 10A–D attached to each end, as shown in FIG. 6. The photomultiplier tubes 10A–D give a voltage pulse proportional to the intensity of the light pulse. The voltage pulse from the photomultiplier tubes are processed by the computer 16, through storage into specific memory banks, to yield information regarding the neutron's two dimensional position and neutron energy. Individual bundles 6 of the strip detector are controlled independently, each with its own photomultiplier tubes, acquisition system and microprocessor. Among other advantages, this construction allows more efficient processing and would allow the system to continue to function if a bundle becomes inoperable.

B. Calculation of Two Dimensional Location of Neutrons

As shown in FIG. 14a the strip detector 74 is constructed of separate bundles 6 stacked in rows one on top of the other. Each strand 20 in a bundle 6 is attached to a photomultiplier tube 10. A neutron striking a strand 20 will cause the photomultiplier tubes attached to the bundle to register and identify a neutron interaction at the y (vertical) coordinate represented by the bundle. The computer 16 registers and stores this data in a specific memory location.

The spatial resolution of the y coordinate is determined by the width of the bundle 6. The optimal width of a bundle will be determined by the specific use of the detector. A wider bundle will yield more counts but less certainty regarding the point of interaction. A narrower bundle yields fewer counts but more certainty. In a preferred embodiment, the bundles 6 will be about 2 cm.–4 cm. wide.

A method by which the tomographic device measures the x position of the neutron interaction includes the following. Light travels from the point of a neutron interaction towards each end of the strand 20. The tomographic device determines the point along the strand 20 where the photon was created by measuring the difference in time for a photon to travel to both ends of the strand. This point is the x coordinate of the interaction. From FIG. 5, assume the light photons travel toward photomultiplier tubes 10A and 10B, to input of or/sum circuit 26 whose or output is fed to the input of time-to-amplitude converter 24. Simultaneously, photons from the interaction travel through the strand toward photomultiplier tubes 10C and 10D, to or/sum circuit 30, whose or output is delayed by delay 42 and goes to the stop input of time-to-amplitude converter 24. Through this measurement the tomographic device calculates the time difference for the photon to travel to both ends of the strand 20.

The time for the pulse to get to the start input of time-to-amplitude converter 24 would be nx/c where x is the x position of the interaction and v is the velocity of light in the scintillation. (Note: v=c/n where c is the velocity of light in a vacuum and n is the index of refraction of the scintillation material.) The time for the start pulse to get to time-to-amplitude converter 22 would be:

$$L/v+x/v \qquad \text{Eq. 1}$$

where L/v is the time delay 42 that has been inserted in the start. A delay 42 is placed in the start input of TAC 24 to normalize the TAC 24 output so that t=0 output corresponds to x=0. Hence, the time difference, t, as measured by time-to-amplitude converter 24 is:

$$t=(L/v+x/v)-(L-x/v)=2x/v \qquad \text{Eq. 2}$$

This is a linear equation with a y intercept of 0 and a slope of 2/v. The tomographic device determines the distance x and hence the point of interaction by measuring the time t through time-to-amplitude converter 24. When x is zero, the time difference will be 0 and when x=L, the length of the bundle, the time difference will be 2/v. FIG. 14a shows that the resolution (or uncertainty) of this measurement constitutes a "virtual detector" 81, as shown in FIG. 14a. For the preferred embodiment as an explosives detection system, this resolution will be approximately 4 cm. The time x/v must be subtracted from the neutron flight time measurement as a correction for the position of the neutron interaction along the bundle 6.

C. Calculation of Neutron Energy

The tomographic device measures neutron energy by measuring the flight time of a neutron over the known flight path. A method includes the following. From FIG. 5, the flight path of each neutron is the distance from the neutron bean target 2 to the bundle 6 on the x-y detector. (The bundles 6 are curved so that the flight path would be the same for all angles of the solid angle subtended by the detector.) From the measured time and the flight path, the tomographic device calculates velocity, $v=d/t$. From the velocity, the tomographic device calculates neutron energy from $E=mv^2/2$. In practice, relativistic equations are used for greater accuracy.

From FIG. 7, time to amplitude converter 22 measures the time of flight for the neutron. The time pick off unit 36 gives the start signal for time to amplitude converter 22 when the neutrons stat at the point source. The output of or/sum circuit 30 provides the stop signal. The stop signal is a sum of the flight time of the neutron and the flight time of the photons in the strand 20. The tomographic device subtract the flight time of the photons in the strand 20 (x/v) when calculating the flight time of the neutrons.

D. Discrimination of Gamma Rays

A scintillation occurs when a neutron scatters from a proton (hydrogen) contained in a strand 20. These recoil protons will stay predominantly in one strand. In contrast, gamma rays will Comptom scatter from electrons in the strand 20. These recoil electrons will travel across several strands. In this way, gamma rays will cause scintillations in two or more strands. FIG. 7 shows that photomultiplier tubes 10A and 10C are fed into an anti-coincidence circuit 34, which determines whether an event caused scintillations in two or more strands. If so, the event was probably due to a gamma ray. If the event caused scintillations in only one strand, the event was probably due to a neutron. Hence, an output from the anti-coincidence circuit signifies a neutron.

E. Increased Neutron Detector Efficiency Without Sacrificing Energy Resolution

Under current technology, neutron detector efficiency is inversely proportional to detector resolution. A thicker bundle 6 will count more neutrons. However, there will be less certainty regarding the location of a neutron interaction. By making the bundle 6 thinner one knows to a greater accuracy the point of interaction. The scintillator should be thin enough so that the time for a neutron to travel the distance across the bundle is about equal to or less than the pulse width of the neutron source, which is less than 1 nanosecond for the preferred embodiment. Hence for many purposes, the thickness of the bundle 6 should be about 1 cm. As shown in FIG. 3, the thickness of the strip detector 74 is 1 cm.

The following technique increases neutron detection efficiency, while preserving the energy measuring capabilities of a thinner detector. In the manner shown in FIG. 5, a bundle 6 is constructed of sixty-four (8×8) strands 20. Each strand in the bundle is about ½ cm. by ½ cm. Each strand 20 is attached to the anode of a multi-anode scintillation detector such as the H4139 Hamamatsu multi-anode photomultiplier tube. The tomographic device can identify the specific strand 20 in which a neutron interaction occurs by means of the anode dedicated to the strand. This detector approximates sixty-four ½ cm. detectors which provide sixty-four individual spectra. Such spectra can be normalized to a single spectra for calculation of neutron energy. Such detector has the increased efficiency of a 4 cm. scintillator but the increased energy resolution of a ½ cm. scintillator. Hence, this detector would require only one fourth of the time that a 1 cm. thick scintillator would require for the same statistics.

4. Array Detector

A. Detection of Fast Neutrons

As shown in FIG. 9, unscattered neutrons passing through the sample 32 will contact one of the scintillator sections 48 of the array detector. Certain neutrons will scatter from hydrogen protons) in a scintillator section 48. The protons will recoil and emit light energy. The scintillator is a fast neutron detector such as BC 404 manufactured by Bicron Corp. The sides of the scintillator sections 48 are opaque to light. A fraction of the light energy is transmitted to the coupler 50, which is constructed as a lens to focus the light into the attached non-scintillating fiber optic cable 52. This light travels down the cable 52 through a fiber optics-anode coupler 54 to an anode 58 of the multi-anode tube 56.

FIG. 12 shows a block diagram of the electronics for one row of the array detector. The multi-anode tube 56 converts the light pulse into a voltage pulse by means of voltage divider 57. The voltage pulse is passed to a discriminator 59, which is dedicated to such individual scintillator segment 48, via signal cabling 60. The discriminator has two outputs. One output goes to the start of the array TAC 84, which is used to measure the neutron energy. The other discriminator output goes to a gate input of the data acquisition and computer 16. Hence, the computer stores all events from each scintillator section 48 in separate segments of its memory for analysis. As shown in FIG. 12, any pulse from any scintillator section 48 can start the TAC 84. The bookkeeping as to which scintillator segment 48 caused the pulse is determined by the respective gate pulse. The pulse is recorded in the dedicated portion of the computer 16 via the gate pulses. The time pick off 86 of the pulsed accelerator provides the stop pulse for TAC 84. The computer 16 processes these pulses, through storage into a specific memory bank, to yield information regarding neutron position and neutron energy. Individual rows of the array detector 72 are controlled independently, each with its own multi-anode photomultiplier tube, acquisition system and microprocessor. This construction allows more efficient processing of data and also would allow the detector to continue to function if one row becomes inoperable.

B. Calculation of Two Dimensional Placement of Neutrons

As shown in FIG. 10, the array detector is constructed of rows and columns of discrete scintillator sections 48. The preferred embodiment of the tomographic device includes twenty-five to fifty individual detectors in a row and as many as fifty rows. The vertical (y) and horizontal (x) positions of a neutron interaction are determined by the respective row and column numbers of the scintillator section.

The spatial resolution of the x and y coordinates are determined respectively by the height and width of the scintillator sections 48. The optimal dimensions will be determined by the specific use of the array detector. A larger scintillator section will yield more counts but less certainty regarding the point of the neutron interaction. In a preferred embodiment, the scintillator sections 48 will be about 2 cm. by 2 cm.

C. Calculation of Neutron Energy

The tomographic device determines neutron energy by measuring the flight time of a neutron over a known distance. A method includes the following. From FIG. 9 the flight path is the distance from the beam target 40 to the scintillator section 48. The scintillator sections 48 are curved so that the flight path is the same for all angles of the solid angle subtended by the detector. All fiber optic cables 52, which connect the scintillator sections to the multi-anode tube 56, are the same length. The tomographic device calculates neutron velocity, v=d/t, from the measured time and the flight path. From the velocity, the tomographic device calculates neutron energy from $E=mv^2/2$. In practice, relativistic equations are used for greater accuracy.

From FIG. 8, the tomographic device measures the time of flight of the neutron through time to amplitude converter 22. Time pick off unit 38 provides the start signal for time to amplitude converter 22 at the time the neutrons start. The or output of or/sum circuit 26 provides the stop signal. The stop signal is a sum of the flight time of the neutron and the flight time of the photons in the cable 52. The tomographic device subtracts the flight time of the photons in the cables 52 when calculating the flight time of the neutrons. In this way, the tomographic device measures neutron energy.

5. Use of Multi-Dimensional Neutron-Computed Tomography to Determine Number Densities of Atoms in a Sample In its single pass option, the invention identifies explosives or contraband by determining the number densities (neutron/$cm^2$) and ratios of H, C, N and O in the neutron beam using pulsed beam neutron time-of-flight techniques. Neutron spectra are taken with and without the sample in the neutron beam. A method of determining neutron attenuation is to determine the ratios of the two spectra on an energy by energy basis (channel by channel) and then take the natural logarithm of these ratios channel by channel. Each point on the curve must satisfy the attenuation equation, which has four unknowns (assuming H, C, N and O are the primary elements in the beam). In one embodiment the tomographic device uses a multichannel analyzer with approximately two hundred fifty channels to record spectra of different energies. There are now two hundred fifty equations and four unknowns. These unknowns are the number densities in neutrons/$cm^2$ of H, N, C, and O contained in the neutron beam. In this way the invention is able to overstate the problem. Regression theory or another method is applied to solve for these unknowns and also for the standard error of these unknowns.

The single pass option determines the number of atoms per square cm. in the neutron beam through the entire width of the suitcase. For example, the ratios obtained with a single pass could indicate a small amount of explosives or a larger amount of non-lethal material. Variability in luggage size further reduces the accuracy of the single pass analysis. In contrast, a tomographic analysis could determine the number densities of atoms per cubic cm. within small incremental volumes in the luggage. For these reasons, the invention was designed to include a tomographic option.

The tomographic device determines the number densities of atoms per $cm^3$ in the neutron beam path for a number of passes at different angles through the sample. These resulting number densities are input into the tomographic program to determine the number densities per cubic centimeter over volume increments through the sample. From these number densities, the tomographic device calculates the ratios C/O, N/O and H/C for each small volume increment in the sample.

The tomographic device does not use input directly from detectors, as in conventional tomography. Instead, the tomographic device uses calculated data as input. The tomographic device calculates number densities in neutrons per $cm^2$ for H, C, N and O for each detector view through the sample. For a single view, there will be as many sets of number densities as there are detectors. For n views there will be n times the number of number densities of a single view. From this data the invention creates four tomographic reconstructions, one each for H, N, C and O. These reconstructions are cuts across the sample in which the number densities of H, C, N, and O are displayed on a two dimensional grid, with the grid dimension being equal to the spatial resolution. Other elements could be included.

The tomographic device was designed to gather and reduce data in proper form for input into commercially available tomogaphraphic programs. This decreases the cost of implementation, allow use of the best program available, and allows the invention to take advantage of future advances in tomographic programs.

This neutron tomographic technique applied by the invention has several major advantages. Total neutron cross sections are used which are in the barn range instead of the millibarn range. This results in greatly increased count rates which give improved statistics per given count time. The number densities can be determined to a few percent during a run of only several seconds. Another major advantage is that the tomographic device determines the number densities of H, C, N, and O in neutrons per $cm^3$ over small volume increments through the sample. This method allows the invention to identify contraband with a high probability of detection. Another major advantage is that the tomographic device is constructed to facilitate tomographic imaging. This allows the tomographic device to create tomographic images of the H, C, N and O concentrations in the interior of a sealed container in a very short time. The method also greatly increases sensitivity for detecting contraband substances.

By obtaining information in this form, the invention optimizes the neural net methods discussed below. These techniques of data reduction, imaging, and analysis provide the tomographic system with the speed and accuracy required for an airport security system.

6. Neural Net Analysis

The invention creates a tomographic image of an unknown sample through data received from its x-y detector. The tomographic image shows the ratios C/O, N/O and H/C in small volume increments through the sample. These volume increments are equal to a single dimension of the x-y detector's spatial resolution cubed. The neural network analyzes the ratios contained in each volume increment to determine whether an explosive is present.

Assume the x-y detector has a spatial resolution of 2 cm. Assume the invention creates a tomographic image of a suitcase which is 100 cm. by 80 cm. by 60 cm. The suitcase has a volume of 480,000 $cm^3$ and so it would be easy to conceal a small explosive inside. The invention provides the average number densities of H, C, N, and O atoms over small volume increments of only 8 $cm^3$ throughout the suitcase. The neural network analyzes this data to identify explosives in each 8 $cm^3$ volume increment. The invention searches all of these small "suitcases" simultaneously, and so the entire analysis is completed in seconds. It would be very difficult to hide an explosive in one of these 8 $cm^3$ suitcases.

In addition to new detection methods, the invention was also designed to allow fast and accurate training by computer simulation. The training takes place on a grid-by-grid basis over the plane of the x-y detector. A training database is created which consists of simulated neutron radiographic scans of small volumes. These volumes are equal to one dimension of the x-y detector's spatial resolution cubed. These simulated volumes contain specific amounts of various substances. The substances include explosives, drugs, and materials commonly found in luggage or which could conceal explosives or drugs.

The density and chemical formula for each substance is obtained from known sources such as the Handbook of Physics and Chemistry. Based upon the density, chemical formula, and amount of the substance, a simulated input case is created showing the number densities and ratios of the atoms in the simulated volume. This simulation is in the form of a radiographic scan of the substances in the volume.

Training methods were developed to allow use of commercially available neural net programs, such as the Explorer program by Neuralware. In this way, the cost of implementing the invention is reduced, a variety of programs are available, and the invention can take advantage of advances in neural network programs. This capability to train the invention's neural net by computer simulation produces very accurate predictions of explosives and allows training to occur very quickly. If a new type of explosive is developed, the tomographic device can be trained to identify the explosive through computer simulated runs and the trained version implemented across the country virtually overnight.

Summary, Ramifications, and Scope

The present invention creates two and three dimensional images of the number densities of atoms in a sample. In its preferred embodiment, the tomographic device detects explosives and other contraband in airport luggage. The tomographic device identifies explosives by determining the ratios per $cm^3$ of H, C, N and O in small volume increments through the luggage. The present invention also includes two new types of fast neutron detectors. The tomographic device also solves certain critical problems in fast neutron radiography and tomography, including detecting fast neutrons in an x-y plane, reducing or eliminating multiple scattering of radiation, discriminating gamma ray from neutron interactions, and applying advanced neural net technology. FIGS. 13e–f show tomographic images of small amounts of explosives and drugs hidden in a sealed suitcase. Clearly, the tomographic device is far more advanced than any existing explosives detection system.

While my above description contains many specifications, these should not be construed as limitations on the scope of the present invention. I have shown and described only the preferred embodiment, simply by way of illustrating the best mode contemplated by me of carrying out the invention. Many other variations are possible without departing from the invention. For example, with regard to the strip detector, the size of the bundles and the size of the individual strands can be varied depending on the parameters of the detector. For a strip that is one meter long, a single strand (block) may be desirable, while for a strip detector three meters long, several strands may be desirable. Instead of photomultiplier tubes, other types of detectors such as CCDs or detectors based on microchannel plates could be used. The invention could be used for determining the composition of a material or for detecting flaws in a sample, or for detecting other materials than explosives, such as narcotics. With regard to the multiple scattering filter, the size of the filter and the shape and sizes of the hollow passages could be varied according to the desired resolution and purposes. Depending upon the size of the multiple correction filter and the cone of radiation from the point source, two conveyor tracks, one on top of the other, could be used to scan two samples at once. If fast scanning of many samples is desired, the turntable device may be constructed to spin a sample for a tomographic image only if the initial radiographic image indicates uncertainty. Accordingly, the scope of the invention should be determined not by the embodiments illustrated, but by the appended claims and their legal equivalents.

The embodiments of the invention and method in which an exclusive property or privilege is claimed are defined below:

1. A method for analyzing neutrons of multiple energies which have passed through a sample to determine the presence or absence *therein* of certain atoms [in specified number densities and ratios,] for purposes of explosives detection or analysis of a sample, comprising the steps of:

(*a*) producing a white neutron beam (a beam of neutrons of multiple energies);

(*b*) determining [the] *a baseline* neutron [attenuation] *intensity* of the white neutron beam without a sample in the path of the beam;

(*c*) directing the white neutron beam through the sample;

(*d*) reducing the multiple scattering of [said] neutrons *by the sample*;

(*e*) measuring the [attenuation] *intensity* of the neutrons which travel through the sample without scattering;

(*f*) comparing the baseline white neutron beam *intensity* directed onto the sample with the *intensity of* unscattered neutrons passing through the sample, and determining [neutron] *therefrom the* attenuation *of the white neutron beam* as a function of neutron energy;

(*g*) comparing the resulting attenuation with known neutron cross-sections;

(*h*) creating a radiographic or tomographic [image showing] *representation of* the number densities [and] *or* ratios of atoms throughout [volume] increments of the sample through [such] *the* comparison *of step* (*g*); and determining whether an explosive or other specific substance is present in any such [volume] increment by comparing the resulting number densities [and] *or* ratios of atoms in said [volume] increments of the sample to known number densities [and] *or* ratios of atoms in explosives or other substance sought to be identified.

2. Apparatus for producing a radiographic/tomographic [view] *representation* of a sample [showing] *based on* the number densities of atoms in *area/*volume increments through [a] *the* sample, [consisting of] *comprising* a first means for producing a beam of white neutrons and directing said beam; a second means for conveying samples into place for exposure to the beam; a third means for directing the beam through the sample; a fourth means for reducing the multiple scattering of neutrons by the sample; a fifth means [of] *for* detecting *unscattered* neutrons *passed through the sample*; a sixth means [of] *for* determining the location in the sample through which [such] *said unscattered* neutrons pass; a seventh means [of] *for* measuring the intensity of neutrons both before and after the sample is placed in the neutron beam; an eighth means [of] *for* comparing the neutrons intensities which reach the detector means without a sample in the neutron beam path with the *unscattered* neutron[s] *intensities which reach the detector means after* passing through the sample; a ninth means [of] *for* determining the number densities or ratios of atoms[, atomic, chemical or physical structure] of the sample through such comparison; a tenth means [of] *for* creating a *radiographic/* tomographic [image] *representation* of the number densities or ratios of atoms[, atomic, chemical or physical structure] of the sample; and an eleventh means [of] *for* comparing said [samples] *number densities or ratios or the sample* with a database of [samples] *number densities or ratios* with known features for features sought to be identified in the unknown sample[s].

3. Apparatus [and means] of claim 2 [whereby] *wherein*

[(A) the first means comprises a neutron accelerator producing a pulsed beam of neutrons of multiple energies from 0.5–15 MeV;]

[(B) the second means comprises a conveyor track system in which samples are conveyed one at a time onto a turntable for purposes of exposure to said neutron beam;]

[(C) the third means comprises a sample turntable in front of a neutron x-y detector so that all portions of said sample are exposed to said beam of neutrons emanating from a neutron point source produced by said accelerator;]

[(D) the fourth means comprises the frustum of a cone placed between said sample and detector, which frustum consists of a neutron attenuating material and is constructed in a dartboard configuration, in which sections of the dartboard alternate between solid segments and hollow passages through such frustum, such that the wall of each hollow passage consists of the outside edge of a solid segment, and the hollow passages are constructed along straight lines from said point source, which lines are perpendicular to said detector, and means for rotating such frustum on its axis;]

[(E)] the fifth means comprises:

(i) one or more scintillating fiber optic strands of a predetermined geometric shape and length, (ii) which fiber optic strands are formed into a predetermined number of discrete bundles [(consisting of one or more of said strands)] stacked linearly one on top of the other;

(iii) with one or more scintillation sensors attached to the end of each bundle, so that [all] *each* fiber optic strand[s are] *is* coupled to a scintillation sensor at each end of the bundle in which the fiber optic strand is located[;]

[(F) the sixth means comprises means of determining the specific bundle containing a fiber optic strand in which a neutron interaction occurs, thereby providing the first two dimensional coordinate of the neutron interaction, and means for calculating the other two dimensional coordinate of said neutron interaction by measuring the difference in time which it takes a photon to travel to opposite ends of such strand, a time delay being place in one end to facilitate calibration;]

[(G) the seventh means comprises means for calculating the energy of a neutron by calculating the time of flight of the neutron from the neutron point source to the interaction on said fiber optic strand;]

[(H) the eighth means comprises a means to determine the neutron attenuation by first measuring and recording in a computer the neutron spectrum with the sample out of the neutron beam and then comparing such data with a measurement of the neutron spectrum with the sample in the neutron beam;]

[(I) the ninth means comprises a means to reconstruct the number densities or ratios of atoms, atomic, physical or chemical structure of the sample by using known total neutron cross sections to determine which elements in the sample and their number densities caused the measured neutron attenuation;]

[(J) the tenth means comprises a means for creating a tomographic image of the number densities of atoms, atomic, physical or chemical structure through volume increments in the sample by determining the neutron attenuation through the sample for several angles through the sample;]

[(K) the eleventh means comprises a database to train a neural network to identify features of volume increments provided in a tomographic image of an unknown sample, using said database containing actual or simulated results of radiographic scans of volume increments equal to the volume increments provided by said tomographic scan, where the volume increments in the database contain known features sought to be identified, so that the neutral network can identify features of a volume increment of said unknown sample when the same features appear in the volume increments of such database].

4. Apparatus [and means] of claim 3, [whereby there is] *wherein each bundle of said fifth means comprises* a plurality of said fiber optic strands [described in the fifth means which are], *said plurality of strands being* routed to two or more scintillation sensors at each end of a bundle in an alternating pattern, so that for any given scintillating strand attached to a given scintillation sensor, all contiguous fiber optic strands are routed to a different scintillation sensor on the same end of the bundle, thereby allowing discrimination of gamma rays from neutron scattering events.

5. Apparatus [and means] of claim 3, in which the scintillation sensor described in the fifth means is a photomultiplier tube and the bundles are approximately 4 centimeters by 4 centimeters thick, comprised of approximately 64 fiber optic strands per bundle, and are greater than one meter in length.

6. Apparatus [and means] of claim 3, in which the scintillation sensor described in the fifth means is a photomultiplier tube and the bundles are comprised of a single bar of scintillating fiber optic material approximately 4 centimeters by 1 centimeter thick, and are equal to or less than one meter in length.

7. Apparatus [and means] of claim 3 is which the scintillation sensors described in the fifth means [of claim 2] have discrete channels[, such as multichannel photomultiplier tubes, microchannel plates, or CCD type detectors,] allowing each strand in a bundle to be attached to a discrete anode or channel, so that the scintillation sensor detects which of said strands registers a scintillation.

8. Apparatus of claim 3 in which:

the fifth means is a neutron detector [constructed as follows: a neutron detector consisting of] *comprising* discrete sections [of a certain size] constructed of a material which scintillates upon interaction with a neutron; each scintillator section [is] *being* connected by a coupler to a non-scintillating fiber optic cable, which coupler is constructed to concentrate the light, and which fiber optic cable is connected to one anode of a multi-anode photomultiplier tube; the photomultiplier tube [is] *being* connected to means for voltage and signaling which in turn is connected to a specific memory bank in a computer, whereby neutrons contacting a scintillator section cause the creation of a photon, which travels down the fiber optic cable to said anode of the photomultiplier tube and is recorded in the memory bank of a computer; [and]

the sixth means comprises a means for identifying the specific scintillator section in which a neutron interaction occurs; and the seventh means comprises a means for measuring the time of flight of a neutron from the [point source] *neutron beam producing means* to a scintillator section, and producing an output signal containing such *time-of-flight* information.

9. Apparatus of claim 3 [whereby] *wherein:* the fifth means comprises a high energy neutron detector [and radiographic/tomographic device,] comprising:

(a) fiber optic scintillating strands of a predetermined geometric shape and length, comprising a material which scintillates when a neutron interaction occurs emitting light, (b) one or more of said scintillating strands are fastened into a discrete bundle of a predetermined width and depth, (c) a predetermined number of said bundles are attached linearly one on top of the other, whereby a detector face with two dimensional coordinates is formed, with one set of coordinates being the separate rows formed by the discrete bundles stacked one on top of the other, and the other set of coordinates being the points along the length of the scintillating strands constituting the bundles, *and*

(d) means for attaching the respective ends of the scintillating strands in each bundle to one or more scintillation sensors attached to each end of each of said bundles, *and*

[(e)] *the sixth means comprises* a means for determining the bundle in which a neutron interaction occurs by means of registering on one or more of said scintillation sensors attached to each end of such bundle, thereby determining one coordinate of the two dimensional location of the neutron on the detector face, and [an apparatus combining or/sum and sum circuits, time to amplitude converters and other common electronic equipment such as discriminators, cabling and power supplies and a specific location in the memory bank of a computer for storing output information,] *means* for measuring the difference in time that it takes a scintillation photon in a said fiber optic strand, caused by a neutron incident on said fiber optic strand, to travel to the opposite ends of such fiber optic strand, and producing an output signal containing such *time-difference* information, thereby allowing calculation of the other coordinate of the two dimensional location of the neutron on the detector face[,]

[(f) the detector is constructed so that the neutrons from said point source strike the detector face approximately perpendicular to the lengths of one or more fiber optic strands constituting each of such bundles; and a combination of or/sum and sum circuits, time to amplitude converters and other common nuclear electronic equipment such as discriminators, cabling and power supplies and a specific location in the memory bank of a computer for storing output information, in order to measure the time of flight of a neutron from the point source to the detector face, and producing an output signal containing such information, thereby allowing calculation of the energy of the neutron].

10. Apparatus of claim 9, [whereby] *wherein* said fiber optic strands are routed to scintillation sensors at each end of a bundle in an alternating pattern, so that for any given scintillating strand attached to a given scintillation sensor, all contiguous scintillating strands are routed to a different scintillation sensor on the same end of the bundle, thereby allowing discrimination of gamma rays from neutron interactions.

11. Apparatus of claim 9 in which the scintillation sensors have discrete channels[, such as multichannel photomultiplier tubes, microchannel plates, or CCD type detectors,] allowing a plurality of strands to be attached to each [anode or] channel of the sensor, or allowing the scintillation sensor to discriminate which specific scintillating strand in a bundle registers a scintillation.

12. Apparatus of claim 9 [having] *wherein the third means comprises* a sample turntable or similar device between the [point] white neutron source and the detector array in order that several neutron radiographic/spectroscopic views may be taken through the sample *within the range* from [0° to 180° or from] 0° to 360°.

13. [In a] *A* device for [analyzing neutrons of multiple energizer means to reduce or eliminate] *reducing or eliminating* the multiple scattering of [radiation emanating from an object] *neutrons* towards a detector *upon the passage of the neutrons through a sample*, [consisting of radiation] *comprising:*

*a filter comprising neutron* attenuating material divided into sections of [a specified geometric shape consisting of] alternating solid segments and hollow passages, which [device] *filter* is placed between [a] *the* sample and [a] *the* detector, and [configured]

*means for rotating or oscillating said filter* so that [(1)] the said hollow passages are rotated or oscillated so as to expose the entire detector surface, at different moments in time, to [radiation] *neutrons* proceeding through the sample, [and (2)] the dimensions of said [device] *filter*, including its width and diameter of its said hollow passages and said segments, [are] *being so* constructed [so] that [radiation] *neutrons* which [is] *are* scattered in said sample will not proceed through a hollow passage to the detector [face] *surface*.

14. [Means] *Apparatus* of claim 13 [for reducing or eliminating the multiple scattering of radiation, consisting of] *wherein said filter comprises* the frustum of a cone divided into alternating segments in a "dart board" configuration around its axis, with sections [consisting of] *comprising* alternating hollow segments and solid passages, [consisting of a radiation attenuating material, and includes a means for rotating said frustum through its axis, and is constructed so that] said hollow passages [lie] *lying* along a straight line proceeding from [a point] *the* neutron source through a sample onto and perpendicular to the [face] *surface* of [a radiation] *the* detector *means*.

15. [Means] *Apparatus* of claim 13 [for reducing the scattering of radiation from an object onto a detector, consisting of a means of exposing] *wherein said means for rotating or oscillating said filter exposes* the entire [face] *surface* of said detector at different moments in time through the rotation or oscillation of solid portions of [radiation] *the neutron* attenuating material and hollow passages in such material.

*16. Apparatus of claim 2, wherein the first means comprises a neutron accelerator producing a pulsed beam of neutrons of multiple energies within the range of approximately 0.5–15 MeV.*

*17. Apparatus of claim 2, wherein the second means comprises a conveyor track system in which samples are conveyed one at a time into a position for exposure to said neutron beam.*

*18. Apparatus of claim 17, wherein the third means comprises:*

*a turntable located at said exposure position for receipt of a sample from said conveyor track system; and*

*means for rotating said sample turntable so that multiple portions of said sample are exposed to said white beam of neutrons.*

*19. Apparatus of claim 2, wherein the fourth means comprises:*

*the frustum of a cone placed between said sample and the detector means, which frustum comprises neutron*

*attenuation material and is constructed in a dartboard configuration, in which sections of the dartboard alternate between solid segments and hollow passages through such frustum, such that the wall of each hollow passage defines the outside edge of a solid segment, and the hollow passages are constructed along straight lines from the neutron source, which lines are substantially perpendicular to said detector means, and*

*means for rotating said frustum about its axis.*

*20. Apparatus of claim 2, wherein the sixth means comprises:*

*means for determining the specific bundle containing a fiber optic strand in which a neutron interaction occurs, thereby providing the first two dimensional coordinate of the neutron interaction; and*

*means for calculating the other two dimensional coordinate of said neutron interaction by measuring the difference in time which it takes a photon to travel to opposite ends of such strand.*

*21. Apparatus of claim 2, wherein the seventh means comprises means for calculating the energy of a neutron by calculating the time of flight of the neutron from the neutron source to the interaction on said fiber optic strand.*

*22. Apparatus of claim 2, wherein the eighth means comprises a means to determine the neutron attenuation by first measuring and recording in a computer the neutron intensity spectrum with the sample out of the neuron beam and then comparing said recorded neutron intensity spectrum with a measurement of the neutron intensity spectrum with the sample in the neutron beam.*

*23. Apparatus of claim 2, wherein the ninth means comprises a means to reconstruct the number densities or ratios of atoms of elements of the sample by using known total neutron cross sections to determine which elements in the sample and their number densities caused the measured neutron attenuation.*

*24. Apparatus of claim 23, wherein the tenth means comprises a means for creating a tomographic representation of the number densities of atoms through volume increments in the sample by determining the neutron attenuation through the sample for several angles of said white neutron beam through the sample.*

*25. Apparatus of claim 2 wherein the eleventh means comprises a neural network trained to identify selected features of area/volume increments provided in a radiographic/tomographic representation of an unknown sample, said selected features corresponding to features of area/volume increments of radiographic/tomographic representations of known samples.*

*26. A method for detecting contraband substances in luggage or other containers, comprising:*

*(a) generating a pulsed white neutron beam having a spectrum of neutron energies over a range sufficient to span the total cross section neutron attenuation peaks characteristic of selected constituent elements of contraband substances;*

*(b) directing the white neutron beam through a container to be investigated;*

*(c) filtering neutrons scattered by the container;*

*(d) detecting unscattered neutrons passed through the container;*

*(e) deriving from said detected neutrons a neutron intensity spectrum for said container as a function of neutron energy;*

*(f) deriving from said container neutron intensity spectrum a neutron attenuation spectrum for said container by comparing said container neutron intensity spectrum with a baseline neutron intensity spectrum derived from neutrons detected without a container interposed in the white neutron beam; and*

*(g) deriving from said container neutron attenuation spectrum an indication of the presence or absence of a contraband substance in said container.*

*27. The method of claim 26, wherein step (g) comprises:*

*comparing said container neutron attenuation spectrum with known total neutron cross sections for said selected elemental constituents to derive the number densities of said selected elemental constituents in the container; and*

*comparing said derived elemental constituent number densities to the known number densities of said selected elemental constituents in contraband substances sought to be detected.*

*28. The method of claim 27, wherein the step of comparing said derived elemental constituent number densities with known elemental constituent number densities comprises:*

*forming ratios of said derived elemental constituent number densities; and*

*comparing said elemental constituent ratios with like ratios of said known elemental constituent number densities.*

*29. The method of claim 28, wherein:*

*said selected elemental constituents comprise hydrogen (H), nitrogen (N), carbon (C) and oxygen (O); and*

*said elemental constituent ratios comprise C/O, N/O and H/C.*

*30. The method of claim 29, wherein said derived elemental constituent ratios are compared with said known elemental constituent ratios by use of a neural network.*

*31. The method of claim 26, further comprising:*

*directing the white neutron beam through the container at a plurality of different angles relative to the container; and*

*repeating steps (c)–(g) at each of said angles.*

*32. Apparatus for detecting contraband substances in luggage or other containers, comprising:*

*(a) means for generating a pulsed white neutron beam having a spectrum of neutron energies over a range sufficient to span the total cross section neutron attenuation peaks characteristic of selected constituent elements of contraband substances;*

*(b) means for directing the white neutron beam through a container to be investigated;*

*(c) means for filtering neutrons scattered by the container;*

*(d) means for detecting unscattered neutrons passed through the container;*

*(e) means for deriving from said detected neutrons a neutron intensity spectrum for said container as a function of neutron energy;*

*(f) means for deriving from said container neutron intensity spectrum a neutron attenuation spectrum for said container by comparing said container neutron intensity spectrum with a baseline neutron intensity spectrum derived from neutrons detected without a container interposed in the white neutron beam; and*

*(g) means for deriving from said container neutron attenuation spectrum an indication of the presence or absence of a contraband substance in said container.*

*33. The apparatus of claim 32, wherein the deriving means of paragraph (g) comprises:*

*means for comparing said container neutron attenuation spectrum with known total neutron cross sections for said selected elemental constituents to derive the number densities of said selected elemental constituents in the container; and*

*means for comparing said derived elemental constituent number densities to the known number densities of said selected elemental constituents in contraband substances sought to be detected.*

*34. The apparatus of claim 33, wherein the means for comparing said derived elemental constituent number densities with known elemental constituent number densities comprises:*

*means for forming ratios of said derived elemental constituent number densities; and*

*means for comparing said elemental constituent ratios with like ratios of said known elemental constituent number densities.*

*35. The apparatus of claim 34, wherein:*

*said selected elemental constituents comprise hydrogen (H), nitrogen (N), carbon (C) and oxygen (O);* and

*said elemental constituent ratios comprise C/O, N/O and H/C.*

*36. The apparatus of claim 35, wherein said means for comparing said derived elemental constituent ratios with said known elemental constituent ratios comprises a neural network.*

*37. The apparatus of claim 32, further comprising means for directing the white neutron beam through the container at a plurality of different angles relative to the container, and having said filtering, detecting and deriving functions of paragraphs (c)–(g) being repeated at each of said angles.*

*38. The apparatus of claim 32, wherein said detecting means comprises a plurality of discrete neutron detectors arranged in an x-y array, each of said discrete detectors being separately coupled to the means for deriving a neutron intensity spectrum.*

*39. The apparatus of claim 38, wherein each of said discrete neutron detectors comprises a scintillator which is sensitive to fast neutrons and which is optically coupled to a photomultiplier tube.*

* * * * *